US007015033B1

(12) United States Patent
Loosmore et al.

(10) Patent No.: US 7,015,033 B1
(45) Date of Patent: Mar. 21, 2006

(54) CO-EXPRESSION OF RECOMBINATION PROTEINS

(75) Inventors: Sheena M. Loosmore, Aurora (CA); Yan-Ping Yang, Toronto (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/577,601

(22) Filed: May 25, 2000

(51) Int. Cl.
*C12N 15/00* (2006.01)
*C12N 15/09* (2006.01)
*C12N 15/63* (2006.01)
*C07H 21/04* (2006.01)

(52) U.S. Cl. ................. 435/320.1; 435/69.1; 435/69.3; 536/23.1; 536/23.2; 536/23.7

(58) Field of Classification Search ............... 435/69.1, 435/69.3, 69.7, 320.1, 252.3, 440, 476; 536/23.1, 536/23.7, 23.2; 530/350, 300, 403; 514/44, 514/2; 424/184.1, 185.1, 190.1, 192.1, 193.1, 424/197.11, 200.1, 234.1, 242.1, 256.1
See application file for complete search history.

(56) References Cited

U.S. PATENT DOCUMENTS

| | | | | |
|---|---|---|---|---|
| 5,474,914 A * | 12/1995 | Spaete | 435/252.3 |
| 5,506,139 A * | 4/1996 | Loosmore et al. | 435/220 |
| 5,656,436 A * | 8/1997 | Loosmore et al. | 435/7.1 |
| 5,869,302 A * | 2/1999 | Loosmore et al. | 435/440 |
| 5,876,733 A | 3/1999 | Barenkamp | 424/256.1 |
| 5,935,573 A | 8/1999 | Loosmore et al. | 424/94.63 |
| 5,939,297 A * | 8/1999 | Loosmore et al. | 435/476 |
| 5,981,503 A * | 11/1999 | Loosmore et al. | 514/44 |
| 6,025,342 A * | 2/2000 | Loosmore et al. | 514/44 |
| 6,147,057 A * | 11/2000 | Loosmore et al. | 514/44 |
| 6,335,182 B1 * | 1/2002 | Loosmore et al. | 424/200.1 |
| 6,361,969 B1 * | 3/2002 | Galeotti | 435/252.3 |

FOREIGN PATENT DOCUMENTS

| | | |
|---|---|---|
| WO | WO 96/03506 | * 2/1996 |
| WO | WO 96/30519 | * 10/1996 |
| WO | WO 99 10375 | 8/1998 |

OTHER PUBLICATIONS

Bass et al., "Multicopy Suppressors of Pre Mutant *Escherichia coli* Include Two HtrA (DegP) Protease Homologs (HhoAB), DksA, and a Truncated RlpA," J. Bacteriology, 178:1154-61 (1996).*
Watson et al. REcombinat DNA, W.H> freeman and Co., New York, 1992.*
Bowie et al., Deciphering the Message in Protein Sequences: Tolerance to Amino Acid Substitutions, Science, vol. 247 (4948), pp. 1306-1310 (1990).*
Spiess et la., Cell, vol. 97, pp. 339-347 (Apr. 1999).*
Faccio et al., The Journal of Biological Chemistry, vol. 275 No. 4, pp. 2581-2588 (Jan. 2000).*
Stedman's Online Medical Dictionary, 27th Edition, defintion of "analog", www. stedmans.com.*
Bluestone, C.D. (1982) Current concepts in otolaryngology. Otitis media in children: to treat or not to treat? N. Engl. J. Med. 30: 1399-1404.
Loosmore, S.M., Yang, Y-P., Oomen, R., Shortreed, J.M., Coleman, D.C., and Klein, M.H. (1998) The *Haemophilus influenzae* HtrA protein is a protective antigen. Immun. 66:899-906.
Pallen, M.J. and Wren, B.W. (1997) The HtrA family of serine proteases. Molec. Microbiol. 26:209-221.
Barenkamp, S.J. and Bodor, F.F. (1990) Development of serum batericidal activity following nontypable *Haemophilus influenzae* acute otitis media. Pediatr. Infect. Dis. 9:333-339.
St. Geme, III, J.W., Kumar, V.V., Cutter, D., and Barenkamp, S.J. (1993) High-molecular-weight proteins of nontypeable *Haemophilus influenzae* mediate attachment to human epithelial cells. Proc. Natl. Acad. Sci. USA 90:2875-2879.
Barenkamp, S.J. (1996) Immunization with high-molecular-weight adhesion proteins of nontypeable *Haemophilus influenzae* modifies experimental otitis media in chinchillas. Infect. Immun. 64:1246-1251.
St. Geme III, J.W. and Grass, S. (1998) Secretion of the *Haemophilus influenzae* HMW1 and HMW2 adesins ainvokves a periplasmic intermediate and requires the HMWB and HMBC proteins. Molec. Microbiol. 27:617-630.
Barenkamp, S.J. and St. Geme III, J.W. (1996) Identification of a second family of high-molecular-weight adhesion proteins expressed by non-typable *Haemophilus influenzae*. Molec. Microbiol. 19:1215-1223.
St. Geme III, J,W,, Cutter, D., and Barenkamp., S.J. (1996) Characterization of the genetic locus encoding *Haemophilus influenzae* type b surface fibrils. J. Bact. 178:6281-6287.
Laemmil, U.K. (1970) Cleavage of structural proteins during the assembly of the head of bacteriophage $T_4$. Nature 227:680-685.
St. Geme III (2001) The Pathogenesis of nontypable *Haemophilus influenzae* otitis media, Vaccine 19, S41-S50.
Andrew Hayhurst and William Harris (1999), *Escherichia coli* Skp Chaperone Coexpression Improves Solubility and Phage Display of Single-Chain antibody Fragments, Protein Expression and Purification 15, 336-343.

(Continued)

*Primary Examiner*—James C Housel
*Assistant Examiner*—Zachariah Lucas
(74) *Attorney, Agent, or Firm*—Sanofi Pasteur Inc.

(57) ABSTRACT

Expression vectors are described which permit the recombinant expression of proteins which essentially contain, in addition to nucleic acid encoding the recombinant protein, nucleic acid encoding a non-proteolytic analog of *Haemophilus* Hin47 protein, with or without leader sequence, or nucleic acid encoding high molecular weight proteins of non-typeable *Haemophilus*, which are hmwB, hmwC or hmwBC.

4 Claims, 26 Drawing Sheets

OTHER PUBLICATIONS

Ellis, J. (1987) Proteins as molecular chaperones. Nature 328:378-379.

Barenkamp, S.J. and St. Geme III, J,W, (1994) Genes encoding high-molecular-weight adhesion proteins of nontypeable *Haemophilus influenzae* are part of gene clusters. Infect. Immun. 62:3320-3328.

Talkington, D.F., Brown, B.G., Tharpe, J.A., Koenig, A., and Russell, H. (1996) Protection of mice against fatal pneumococcal challenge by immunization with pneumococcal surface adhesin A (PsaA). Microb. Pathog. 21:17-22.

Caspers, P., Stieger, M., and Burn, P. (1994) Overproduction of bacterial chaperones improves the solubility of recombinant protein tyrosine kinases in *Escherichia coli*. Cell Mol Biol (Noisy-le-grand) 40(5):635-44.

Nishihara, K., Kanemori, M., Kitagawa, M., Tanagi, H., and Yura, T. (1998) Chaperone coexpression plasmids: differential and synergistic roles of DnaK-Dna-GrpEL-GroES in assisting folding of an allergen of Japanese cedar pollen, Cryj2, in *Escherichia coli*. Appl. Environ Microbiol 64(5): 1694-9.

Crowl, R. et al., (1985) Versatile expression vectors for high-level synthesis of cloned gene products in *Escherichia coli*, Gene, 38:31-38.

Lobigs M, Chelvanayagam G, Müllbacher, A, "Proteolytic processing of peptides in the lumen of the endoplasmic reticulum for antigen presentation by major histocompatibility class I", Eur. J. Immunol., vol. 30, pp. 1496-1506 (May 2000).

Bernstein HD, "The biogenesis and assembly of bacterial membrane proteins", Current Opin. Microbiol., vol. 3, No. 2, pp. 203-209 (Apr. 2000).

Poquet I, Saint V, Seznec E, Simoes N, Bolotin A, Gruss A, "HtrA is the unique surface housekeeping protease in *Lactococcus lactis* and is required for natural protein processing", Mol. Microbiol., vol. 35, No. 5, pp. 1042-1051 (Mar. 2000).

Noone D, Howell A, Devine KM, "Expression of ykdA, encoding a *Bacillus subtilis* homologue of HtrA, is heat shock inducible and negatively autoregulated", J. Bacteriol., vol. 182, No. 6, pp. 1592-1599 (Mar. 2000).

Fakruddin JM, Biswas S, Sharma YD, "Metalloprotease activity in a small heat shock protein of the human malaria parasite Plasmodium vivax", Infection and Immunity, vol. 68, No. 3, pp. 1202-1206 (Mar. 2000).

Kim KI, Park SC, Kang SH, Cheong GW, Chung CH, "Selective degradation of unfolded proteins by the self-compartmentalizing HtrA protease, a periplasmic heat shock protein in *Escherichia coli*", J. Mol. Biol., vol. 294, pp. 1363-1374 (Dec. 1999).

Forsdyke DR, "Heat shock proteins as mediators of aggregation-induced 'danger' signals: implications of the slow evolutionary fine-tuning of sequences for the antigenicity of cancer cells", Cell Stress & Chaperones, vol. 4, No. 4, pp. 205-210 (Dec. 1999).

* cited by examiner

Construction of JB-3120-2, a plasmid containing T7 *H91A hin47* (+ leader)

FIG.1B

Oligonucleotide primers to PCR amplify the Nde I-Pvu I fragment encoding the leader sequence of HtrA.

```
         Nde I
            M  K  K  T  R  F  V  L  N  S                                SEQ ID No.2
5'  GGCCG[CATATG]AAAAAAACACGTTTTGTACTAAATAGT      3'   6931.SL    SEQ ID No.1


                      Pvu I
     F  K  F  F  F  G  D  R  F  A  E  Q                                 SEQ ID No.5
    TTTAAATTCTTCTTTGG[CGATCG]TTTTGCCGAACAA                              SEQ ID No.4
3'  AAATTTAAGAAGAAACCGCTAGCAAAACGGCTTGTT            5'   6932.SL    SEQ ID No.3
```

Production of H91A Hin47 +/- leader

1. H91A Hin47 (- leader) $t_0$
2. H91A Hin47 (- leader) $t_4$
3. H91A Hin47 (+ leader) $t_0$
4. H91A Hin47 (+ leader) $t_4$ Purification of H91A Hin47 (+ leader) from *E. coli*

Extraction of H91A Hin47 +/- leader, produced in E. coli

1. Pre-stained markers

2. *E. coli* whole cells

3. Soluble proteins in 50mM Tris-HCl extraction

4. Soluble proteins in Tris/EDTA/Triton-100 extraction

5. Remaining pellets

Construction of DS-2342-2-2, a plasmid containing T7 *H91A hin47* and *T7 V38 hia*

Production of V38 rHia andH91A Hin47 when co-expressed

1. V38 rHia and H91A Hin47 $t_0$
2. V38 rHia and H91A Hin47 $t_4$
3. V38 rHia alone $t_4$ Purification of H91A Hin47 and V38 rHia from *E. coli*

1. Prestained molecular weight markers
2. *E. coli* whole cell lysate
3. Tris/NaCl extract
4. Tris/ Triton X-100 / EDTA extract
5. Tris/ OG extract
6. DEAE flow-through
7. HTP flow-through
8. Purified H91A Hin47
9. Purified rHia Construction of JB-3134-1-1, a plasmid containing T7 H91A hin47 (-leader) and T7 S44 hia PBR T7 H91A Hin47 (-L)/T7 S44 hia/cer/kanR Construction of JB-3145-1, a plasmid containing T7 H91A hin47 (+ leader) and T7 S44 hia Production of S44 rHia and H91A Hin47 (+/-L), when co-expressed.

1 2 3 4 5 6

200 kDa
116
97.4
66
45
31

← S44 rHia

← H91A Hin47

1. H91A Hin47 (-L) $t_0$
2. H91A Hin47 (-L) $t_4$
3. H91A Hin47 (+L) $t_4$
4. S44 rHia $t_4$
5. H91A Hin47 (-L) + S44 rHia $t_4$
6. H91A Hin47 (+L) + S44 rHia $t_4$

Construction of JB-3073R-1, a plasmid containing T7 psaA (+ leader) and T7 H91A hin47

FIG.12B

Oligonucleotide primers for PCR amplify psaA(+native leader)

Sense:

```
                Nde I
                  M  K  K  L  G  T  L  L  V  L                        SEQ ID No.27
5'  CGGGATCCCATATGAAAAAATTAGGTACATTACTCGTTCTC    3'   6850.SL   SEQ ID No.26
```

Antisense:

```
    CATGTGAGCTGGCGTTTTTTAAGCTTGGCC                                    SEQ ID No.29
3'  GTACACTCGACCGCAAAAAATTCGAACCGG               5'   6852.SL   SEQ ID No.28
                          Hind III
```

Construction of JB-3090-1 and JB-3090-7, plasmids containing T7 psaA (-leader) and T7 H91A hin47

FIG.13B

Oligonucleotide primers to PCR amplify psaA (- leader)

Sense:

```
             M  C  A  S  G  K  K  D  T                       SEQ ID No.31
5'  CGGGATCCCATATGTGTGCTAGCGGAAAAAAAGATACA    3'   6851.SL   SEQ ID No.30
```

Antisense:

```
    CATGTGAGCTGGCGTTTTTTAAGCTTGGCC                           SEQ ID No.29
3'  GTACACTCGACCGCAAAAAATTCGAACCGG            5'   6852.SL   SEQ ID No.28
                        Hind III
```

Production of rPsaA +/- leader and H91A Hin47, when co-expressed.

1. H91A Hin47 and rPsaA (+ leader), < > orientation $t_0$
2. H91A Hin47 and rPsaA (+ leader), < > orientation $t_4$
3. H91A Hin47 and rPsaA (+ leader), > > orientation $t_4$
4. H91A Hin47 and rPsaA (- leader), > > orientation $t_4$ Purification of H91A Hin47 and rPsaA from *E. coli*

Purification of H91A Hin47 and rPsaA from E. coli

1. Pre-stained molecular weight markers
2. *E. coli* whole cell lysate
3. Soluble proteins in 50mM Tris-HCl, pH 8.0 extraction
4. DEAE-Sephacel column
5. HTP column
6. Sartobind Q membrane

FIG.17B

Oligonucleotide primers for PCR amplification of Nde I-EcoR I 5′ *hmwB* fragment.

coding strand:

```
            Nde I
               M  K  N  I  K  S  R  L  K  L                        SEQ ID No:7
5′   GGCCGCATATGAAAAATATAAAAAGCAGATTAAAACTC   3′   7072.SL         SEQ ID No:6
```

non-coding strand:

```
                                    EcoR I
      G  R  Q  W  F  D  L  R  E  F  N  M  A                        SEQ ID No:10
     GGTCGTCAGTGGTTCGATTTGCGTGAATTCAATATGGCA                        SEQ ID No:9
3′   CCAGCAGTCACCAAGCTAAACGCACTTAAGTTATACCGT   5′   5950.SL         SEQ ID No:8
```

Construction of plasmid containing T7 hmwB

FIG.18B

Oligonucleotides for construction of the Hind III-BamH I 3′ *hmwB* fragment.

```
Hind III
 S  L  D  A  F  V  A  R  R  F  A  N  A  N  S  D  N  L  N  G  N  K  K  R  T  S  S  P  T  T...
AGCTTAGATGCTTTTGTTGCTCGTCGCTTTGCAAATGCCAATAGTGACAATTTGAATGGCAACAAAAAA          ...
                                                      CGCACAAGCTCACCTACAAC...
      ... F  W  G  R  L  T  F  S  F  *  *                          SEQ ID No:13
      ...                                          7073.SL          SEQ ID No:11
      ...CTTCTGGGGTAGATTAACATTCAGTTTCTAATAG       7074.SL          SEQ ID No:12

  ATCTACGAAAACAACGAGCAGCGAAACGTTTACGGTTATCACTGTTAAACTTACCGTTGTTTTTGCGTGTTCGAG     ...
                                                                   TGGATGTTG...
                            ...
                                                   7076.SL          SEQ ID No:15
      ...
      ...GAAGACCCCATCTAATTGTAAGTCAAAGATTATCCTAG    7075.SL          SEQ ID No:14
                                        BamH I
      ...
```

Construction of a plasmid containing T7 hmwC

FIG.19B

Oligonucleotide primers for PCR amplification of Nde I-Xho I 5′ *hmwC* fragment.

coding strand:

```
            Nde I
              M  T  K  E  N  L  Q  S  V  P                        SEQ ID No:17
5′    GGCCGCATATGACAAAAGAAAATTTACAAAGTGTTCCA    3′    7077.SL    SEQ ID No:16
```

non-coding strand:

```
                    Xho I
      S  T  S  M  I  A  A  R  E  K  F  Y                          SEQ ID No:20
     TCAACTTCAATGATTGCTGCTCGAGAAAAATTCTAT                         SEQ ID No:19
3′   AGTTGAAGTTACTAACGACGAGCTCTTTTTAAGATA    5′    7078.SL        SEQ ID No:18
```

FIG.19C

Oligonucleotides for construction of Hind III-BamH I 3′ *hmwC* fragment.

```
Hind III
  L  F  T  G  D  P  R  P  L  G  K  I  L  L  K  K  T  N  E  W...
AGCTTTTTACAGGCGACCCTCGTCCATTGGGCAAAATA                     ...
                                      CTGCTTAAGAAAACAAATGAATG...
        ... K  R  K  H  L  S  K  K  *  *                                SEQ ID No:23
        ...                                                   7079.SL   SEQ ID No:21
        ...GAAGCGGAAGCACTTGAGTAAAAAATAATAG                    7080.SL   SEQ ID No:22

   AAAATGTCCGCTGGGAGCAGGTAACCCGTTTTATGACGAATTC             ...
                                              TTTTGTTTACTTAC...
                                                           ...
                                                              7082.SL   SEQ ID No:25
        ...                                                   7081.SL   SEQ ID No:24
        ...CTTCGCCTTCGTGAACTCATTTTTTATTATCCTAG
                                       BamH I
        ...
```

CO-EXPRESSION OF RECOMBINATION PROTEINS

FIELD OF THE INVENTION

The present invention relates to the fields of molecular biology, biochemistry and vaccinology, in particular, to the co-expression of recombinant proteins.

BACKGROUND TO THE INVENTION

Recombinant proteins expressed from *E. coli*, are often made as insoluble inclusion bodies. While the purification of inclusion bodies is relatively straightforward and can lead to a >90% purification of the recombinant protein, the resulting protein is often denatured and may be biologically inactive. In some instances, it may be advantageous to overproduce a recombinant protein in a soluble form. Recombinant proteins can also be degraded by host proteases. Expression of recombinant proteins in the presence of particular proteins, such as potential molecular chaperones, may have the effect of protecting them from degradation and ensure correct folding. In other instances, it may be useful to produce two vaccine components, from different organisms, in the same production cycle. Co-expression of recombinant proteins encoded on genes from multiple organisms can lead to improved production time and costs.

Otitis media is the most common illness of early childhood, with 60 to 70% of all children of less than 2 years of age experiencing between one and three ear infections (ref. 1, various references are referred to in parenthesis to more fully describe the state of the art to which this invention pertains. Full bibliographic information for each citation is found at the end of the specification, immediately preceding the claims. The disclosure of these references are hereby incorporated by reference into the present disclosure). Chronic otitis media is responsible for hearing, speech and cognitive impairments in children. In the United States alone, treatment of otitis media costs between 1 and 2 billion dollars per year for antibiotics and surgical procedures, such as tonsillectomies, adenoidectomies and the insertion of tympanostomy tubes. It is estimated that an additional $30 billion is spent per annum on adjunct therapies, such as speech therapy and special education classes. The disease is caused by bacterial and/or viral infections, and many of the bacteria are becoming antibiotic resistant. Infection with *Streptococcus pneumoniae* accounts for about 50% of bacterial disease, while non-typeable *Haemophilus influenzae* (NTHi) infections account for about 30%, and *Moraxella catarrhalis* is responsible for about 20% of acute otitis media. An effective prophylactic vaccine against otitis media is thus desirable.

When under environmental stress, such as high temperature, organisms overproduce stress response or heat shock proteins (hsps). In some instances, hsps have also been demonstrated to be molecular chaperones (ref. 2). The bacterial HtrA or DegP heat shock proteins are expressed under conditions of stress and the *H. influenzae* HtrA protein has been shown to be a partially protective antigen in the intrabulla challenge model of otitis media (ref. 3). The HtrA proteins are serine proteases and their proteolytic activity makes them unstable. In addition, as components of a multi-component vaccine, the wild-type HtrA protein degrade admixed antigens. The site-directed mutagenesis of the *H. influenzae* htrA gene (termed hin47) and the properties of the mutants have been fully described in U.S. Pat. No. 5,506,139 (Loosmore et al.), assigned to the assignee hereof and the disclosure of which is incorporated herein by reference. The non-proteolytic HtrA analogue, H91A Hin47, has been shown to be a protective antigen in the intrabulla chinchilla model of otitis media (ref 3). The mature H91A Hin47 protein is produced at 40 to 50% of total *E. coli* protein, in a soluble form. It may also be produced with its leader sequence, at a level of 20 to 30% of total *E. coli* protein. In this form, it may function as a molecular chaperone, anchored in the periplasmic membrane (ref 4).

During natural infection by NTHi, surface-exposed outer membrane proteins that stimulate an antibody response are potentially important targets for bactericidal and/or protective antibodies and are therefore potential vaccine candidates. Barenkamp and Bodor (ref. 5) demonstrated that convalescent sera from children suffering from otitis media due to NTHi, contained antibodies to high molecular weight (HMW) proteins. About 70 to 75% of NTHi strains express the HMW proteins, and most of these strains contain two gene clusters termed hmw1ABC and hmw2ABC (refs. 6, 7). The HMWA proteins have been demonstrated to be adhesins mediating attachment to human epithelial cells (ref 8). Immunization with a mixture of native HMW1A and HMW2A proteins resulted in partial protection in the chinchilla intrabulla challenge model of otitis media (ref 9). The production yields of native HMW proteins from *H. influenzae* strains are very low, but a method for producing protective recombinant HMW (rHMW) proteins has been described in copending U.S. patent application Ser. No. 09/167,568 filed Oct. 7, 1998 (WO 00/20609), assigned to the assignee hereof and the disclosure of which is incorporated herein by reference. The HMWB and HMWC proteins are thought to function as molecular chaperones, responsible for the correct processing and secretion of the HMWA proteins (ref 10).

A second family of high molecular weight adhesion proteins has been identified in about 25% of NTHI and in encapsulated *H. influenzae* strains (refs. 11, 12, 13). The NTHi member of this second family is termed *Haemophilus Influenzae* adhesin or Hia, and the homologous protein found in encapsulated strains is termed *Haemophilus influenzae* surface fibril protein or Hsf. The hia gene was originally cloned from an expression library using convalescent sera from an otitis media patient, which indicates that it is an important immunogen during disease. Production of the full-length recombinant Hia protein in *E. coli* appears to be toxic to the host, so a series of N-terminally truncated proteins was made as described in U.S. Pat. No. 6,335,182 and in PCT Patent Application No. PCT/CA00/00289 filed Mar. 16, 2000, both assigned to the assignee hereof and the disclosures of which are incorporated herein by reference. The V38 rHia protein was chosen for further development as a vaccine, but it was found that the first 6 amino acids of this protein were deleted from a portion of the product during synthesis in *E. coli*, leading to a mixture of V38 rHia and S44 rHia. When an expression construct was developed to produce the S44 rHia, it was found that the N-terminus was stable, with only S44 rHia product being made. The rHia products appear as a doublet on SDS-PAGE when expressed alone. However, when co-expressed with H91A Hin47, the S44 rHia is produced as a single band, as described below.

The *S. pneumoniae* antigen, pneumococcal surface adhesin A or PsaA, is a protective antigen in an animal model (ref 14), which is produced in high yield from *E. coli* as a 37 kDa protein. The protein may be produced as a lipoprotein if the psaA gene contains a sequence encoding a lipoprotein leader sequence, or as a soluble protein if the gene encodes the mature protein. The protein and the encoding nucleotide sequence are described in U.S. Pat. No. 5,854,466, the disclosure of which is incorporated herein by reference. When co-expressed with H91A Hin47, both proteins are produced in high yield, as described below. They may be separated by hydroxylapatite (HTP) column chromatography during purification, resulting in the high level production of two vaccine components from different organisms, as described herein.

The over-production of *E. coli* chaperone proteins DnaK, DnaJ and GrpG (Hsp70) or GroEL and GroES (Hsp60) results in increased solubility of recombinant human protein kinases Csk, Fyn or Lck (ref 15). These chaperones have also been shown to aid in the refolding of an allergen (Japanese cedar pollen) in *E. coli* (ref. 16). The *E. coli* Skp chaperone has also been used to increase the solubility of recombinant single-chain antibody fragments when co-expressed in *E. coli* (ref. 17). All these systems use a native *E. coli* chaperone to aid in the solubility and folding of recombinant proteins in *E. coli*. The present invention, for the first time, uses a heterologous protein as the chaperone.

SUMMARY OF THE INVENTION

The present invention is directed to the expression of recombinant protein and expression vectors for utilization therein. In one feature of the present invention, such expression is effected in conjunction with expression of non-proteolytic analogs of *Haemophilus* Hin47 and in another feature of the present invention, such expression is effected in conjunction with expression of a high molecular weight protein of non-typeable *Haemophilus* which is hmwBC, hmwB or hmwC.

Accordingly, in one aspect of the present invention, there is provided an expression vector, comprising a nucleic acid molecule encoding a non-proteolytic analog of a Hin47 protein of a strain of *Haemophilus* including a portion thereof encoding the leader sequence for said non-proteolytic analog, and a promoter operatively connected to said nucleic acid molecule to direct expression of said non-proteolytic analog of a Hin47 protein having said leader sequence in a host cell.

In the various aspects of the invention involving a non-proteolytic analog of Hin47 protein, such analog may be a mutation of natural Hin47 protein in which at least one amino acid selected from the group consisting of amino acids 91, 121 and 195 to 201 of natural Hin47 protein has been deleted or replaced by another amino acid. Preferably, the analog has histidine 91 replaced by alanine. This specific analog is termed H91A Hin47.

The vector may be a plasmid vector which may be one having the identifying characteristics of plasmid JB-3120-2 as seen in FIG. 1A, such identifying characteristics being the nucleic acid sequences and restriction sites identified therein.

In accordance with another aspect of the present invention, there is provided an expression vector for expression of a recombinant protein in a host cell, comprising a nucleic acid molecule encoding a non-proteolytic analog of a *Haemophilus* Hin47 protein, at least one additional nucleic acid molecule encoding a recombinant protein, and at least one regulatory element operatively connected to said first nucleic acid molecule and said at least one additional nucleic acid molecule to effect expression of at least said recombinant protein in the host cell.

In one embodiment, the nucleic acid molecule encoding the non-proteolytic analog of a Hin47 protein includes a portion thereof encoding the leader sequence of the non-proteolytic analog, or such portion may be absent.

The at least one additional nucleic acid molecule may encode a Hia or Hsf protein of a strain of *Haemophilus influenzae*, specifically a Hia protein which is N-terminally truncated. The N-terminal truncation may be S44 or V38. The construction of such N-terminal truncations is described below.

The vector may be a plasmid vector, which may be one having the identifying characteristics of plasmid DS-2542-2-2 as seen in FIG. 5 or of plasmid JB-3145-1 seen in FIG. 10, for expression of N-terminally truncated Hia proteins. Such identifying characteristics are the nucleic acid sequences and restriction sites seen in the respective Figures.

The at least one additional nucleic acid molecule may encode a PsaA protein of a strain of *Streptococcus pneumoniae*. The vector may be a plasmid vector having the identifying characteristics of plasmid JB-3073R-1 as seen in FIG. 12 or of plasmid JB-3090-1 or JB-3090-7, as seen in FIG. 13, and expressing the PsaA protein. Such identifying characteristics are the nucleic acid sequences and restriction sites seen in the respective Figures.

The expression vector provided in this aspect of the present invention may be utilized in the generation of a recombinant protein by expression from a suitable host cell, such as *E. coli*. Accordingly, in another aspect of the present invention, there is provided a method for expressing at least one protein, which comprises providing a first nucleic acid molecule encoding a non-proteolytic analog of a Hin47 protein of *Haemophilus*; isolating at least one additional nucleic acid molecule encoding a protein other than Hin47; introducing the first nucleic acid molecule and the at least one additional nucleic acid molecule into a cell to produce a transformed cell; and growing the transformed cell to produce at least one protein. The nucleic acid molecules and regulatory elements may be incorporated into any of the specific expression vectors discussed above.

As noted above, one feature of the present invention involves vectors based on nucleic acid encoding high molecular weight (protein of a non-typeable strain of *Haemophilus*. Accordingly, in accordance with a further aspect of the present invention, there is provided an expression vector, comprising a nucleic acid molecule encoding a high molecular weight protein of a non-typeable strain of *Haemophilus* selected from the group consisting of hmwB and hmwC, and a promoter operatively connected to said nucleic acid molecule to direct expression of said high molecular weight protein in a host cell.

The vector may be a plasmid vector which may have the identifying characteristics of IN-137-1-16 shown in FIG. 18A or of pT7 hmwC shown in FIG. 19A, such identifying characteristics being the nucleic acid sequences and restrictions sites identified in the respective Figures.

The vectors, along with corresponding vectors including the hmwBC gene, may be used to construct expression vectors for the recombinant expression of proteins in a host cell. Accordingly, a yet further aspect of the present invention provides an expression vector for expression of a recombinant protein in a host cell, comprising a nucleic acid molecule encoding a high molecular weight (HMW) protein of a non-typeable strain of *Haemophilus* selected from the group consisting of hmwBC, hmwB and hmwC, at least one additional nucleic acid molecule encoding the recombinant protein, and at least one regulatory element operatively connected to said first nucleic acid molecule and said at least one additional nucleic acid molecule to effect expression of at least said recombinant protein in the host cell.

In the latter vector, the at least one additional nucleic acid molecule may be inserted into a plasmid having the identifying characteristics of IN-52-1-13 as shown in FIG. 17A, or of IN-137-1-16 shown in FIG. 18A, or pT7 hmwC shown in FIG. 19A, under the control of the regulatory element(s). Such identifying characteristics are the nucleic acid molecules and restriction sites identified in the respective Figures.

BRIEF DESCRIPTION OF THE DRAWINGS

The present invention will be further understood from the following description with reference to the accompanying drawings, in which:

FIG. 1B describes the oligonucleotides used for PCR amplification of the sequence encoding the leader. Sense strand (6931.SL) SEQ ID No: 1, encoded amino acid sequence SEQ ID No: 2; anti-sense strand (6932.SL) SEQ ID No: 3, complementary strand SEQ ID No: 4, encoded amino acid sequence SEQ ID No: 5.

FIG. 12B shows the oligonucleotide primers used to amplify psaA (+leader). Sense strand (6850.SL), SEQ ID No: 26, encoded amino acid sequence, SEQ ID No: 27; anti-sense strand (6852.SL) SEQ ID No: 28, complementary strand, SEQ ID No: 29.

FIG. 13B shows the oligonucleotide primers used to amplify psaA (−leader). Sense strand (6851.SL), SEQ ID No: 30, encoded amino acid sequence, SEQ ID No: 31; anti-sense strand (6852.SL) SEQ ID No: 28, complementary strand, SEQ ID No: 29.

FIG. 17B illustrates the oligonucleotide primers used to PCR amplify the Nde I-EcoR I 5' hmwB fragment. Sense strand (7072.SL) SEQ ID No: 6, encoded amino acid sequence SEQ ID No: 7; anti-sense strand (5950.SL) SEQ ID No: 8, complementary strand SEQ ID No: 9, encoded amino acid sequence SEQ ID No: 10.

FIG. 18B illustrates the oligonucleotides used for construction of the Hind III-BamH I 3' hmwB fragment. 7073.SL, SEQ ID No: 11; 7074.SL, SEQ ID No: 12; encoded amino acid sequence, SEQ ID No: 13; 7075.SL, SEQ ID No: 14, 7076.SL, SEQ ID No: 15.

FIG. 19B illustrates the oligonucleotide primers used to PCR amplify the Nde I-Xho I 5' hmwC fragment. Sense strand (7077.SL) SEQ ID No: 16, encoded amino acid sequence, SEQ ID No: 17; anti-sense strand (7078.SL) SEQ ID No: 18, complementary strand SEQ ID No: 19, encoded amino acid sequence SEQ ID No: 20.

FIG. 19C illustrates the oligonucleotides used to construct the Hind III-BamH I 3' hmwC fragment. 7079.SL, SEQ ID No.: 21; 7080.SL, SEQ ID No: 22; encoded amino acid sequence, SEQ ID No: 23; 7081.SL, SEQ ID No: 24; 7082.SL, SEQ ID No: 25.

GENERAL DESCRIPTION OF THE INVENTION

For clarity of disclosure, and not by way of limitation, the detailed description of the invention is divided into the following sections:

1. Production of Recombinant *H. Influenzae* H91A Hin47 Protein with its Leader Sequence.

The native bacterial HtrA protein (H. influenzae Hin47) is a stress response protein located in the periplasmic membrane and responsible for survival of the organism under stress conditions, such as high temperature. It is a serine protease that degrades improperly folded de novo synthesized proteins. In the aforementioned U.S. Pat. No. 5,506,139, there is described the production of high yield (40 to 50% of total *E. coli* proteins), soluble, mature wild-type recombinant H influenzae Hin47 protein from *E. coli*. The rHtrA (rHin47) protein had serine protease activity, which rendered it unstable after purification. Several analogues of Hin47 were generated by site-directed mutagenesis and the H91A Hin47 recombinant protein was found to be stable, of high yield, and protective in animal models. It had lost all measurable serine protease activity. When produced as the soluble mature protein, H91A Hin47 seemed to increase the solubility of co-produced proteins, a property which can be advantageous, as described below.

Figure 4:
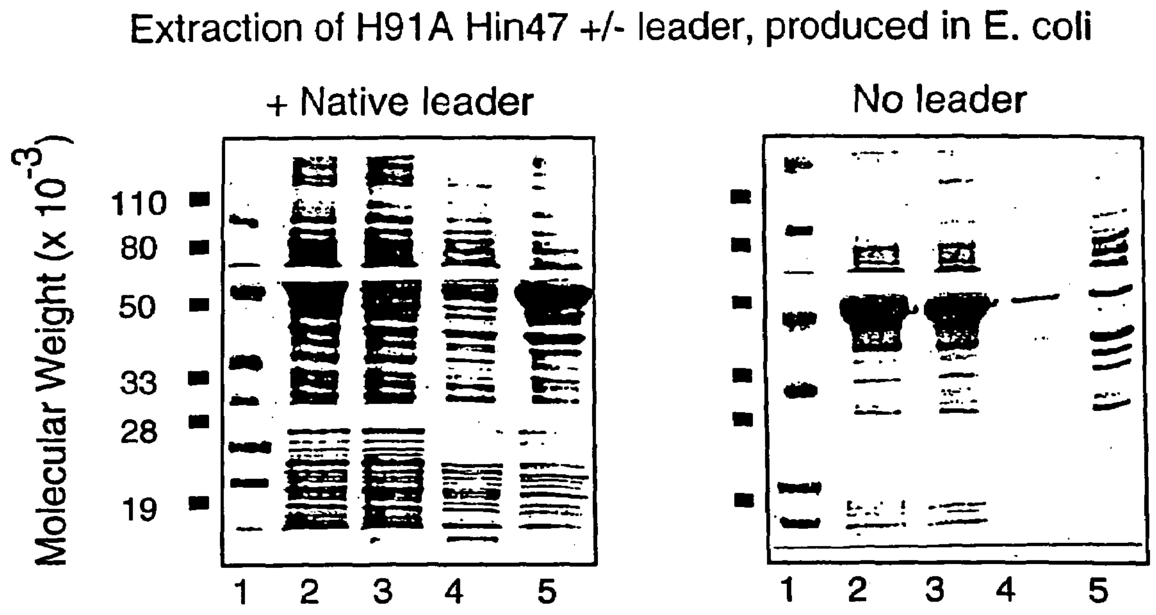
FIG. 4, having Panels A and B, contains a gel analysis of the extraction of H91A Hin47 with (Panel A) or without (Panel B) its leader sequence. Lane 1, prestained protein molecular weight markers; lane 2, *E. coli* whole cell lysates; lane 3, soluble proteins in 50 mM Tris-HCl, pH 8.0 extraction; lane 4, soluble proteins in 50 mM Tris-HCl, pH 8.0/0.5% Triton X-100/10 mM EDTA extraction; lane 5, pellets after the two extractions.

Stress response proteins may function as chaperones, serving to stabilize other expressed proteins. The H91A Hin47 protein has been produced with its endogenous leader sequence in an attempt to localize it to the periplasmic membrane and mimic the HtrA chaperone function. Since the endogenous serine protease activity has been ablated, it was hoped that H91A Hin47 might stabilize co-produced proteins in *E. coli*. The H91A Hin47 (+leader) protein was made at 20 to 25% of total *E. coli* protein (FIG. 2) and was found to be insoluble after extraction with Triton X-100, suggesting that it was expressed either as a membrane-bound protein or inclusion bodies (FIG. 4).

2. Production of Recombinant *H. Influenzae* Hia Protein in the Presence of H91A Hin47, with or without a Leader Sequence.

Figure 6:
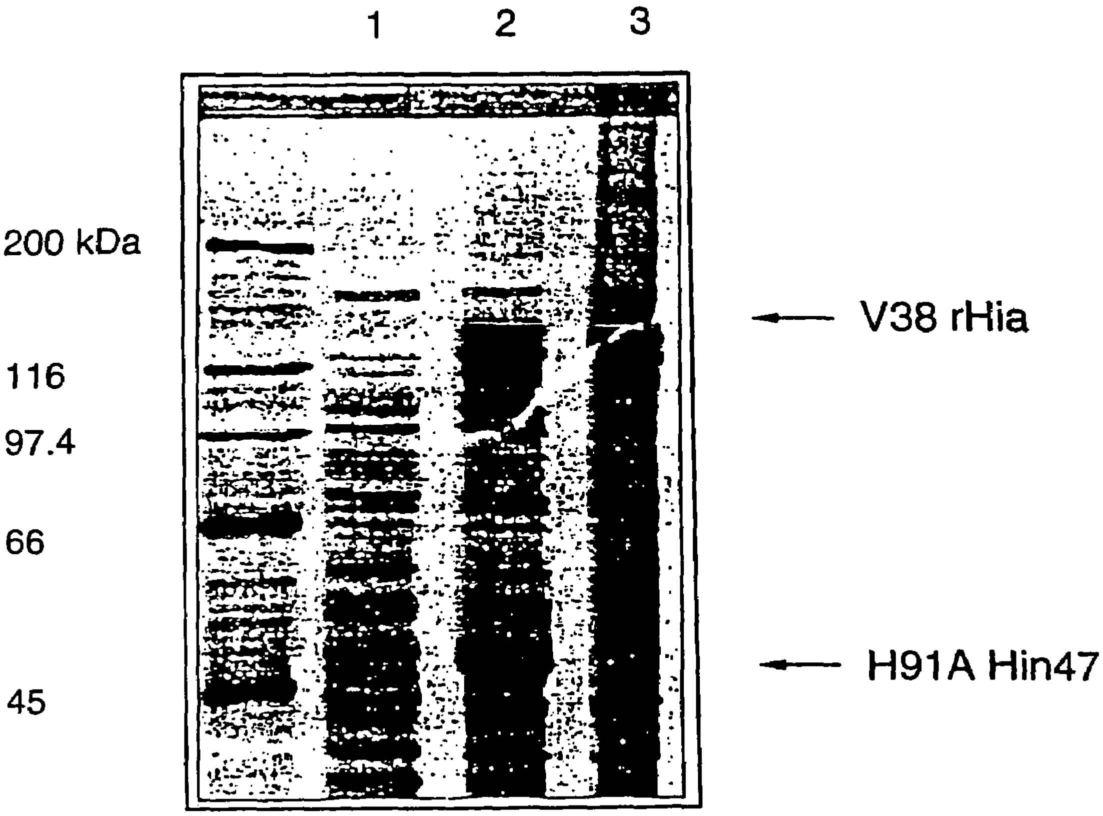
FIG. 6 contains an SDS-PAGE analysis of the production of V38 rHia and H91A Hin47, when co-expressed from the same plasmid. Lane 1, V38 rHia+H91A Hin47, $t_0$; Lane 2, V38 rHia+H91A Hin47, t4; V38 rHia, $t_4$.
Figure 8:
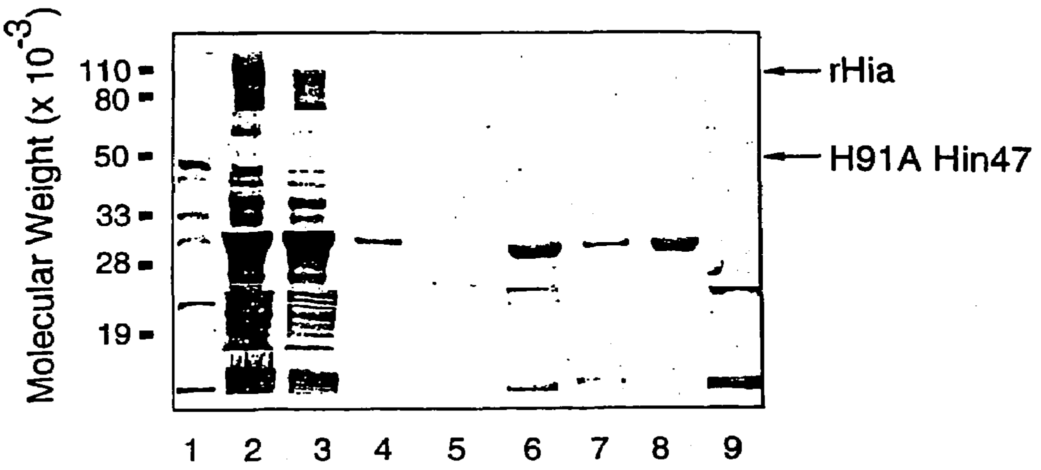
FIG. 8 contains an SDS-PAGE analysis of the purification of V38 rHia after co-expression with H91A Hin47. Lane 1, Prestained molecular weight markers; lane 2, *E. coli* cell lysate; lane 3, soluble proteins after 50 mM Tris-HCl, pH 8.0/0.1 M NaCl extraction; lane 4, soluble proteins in 50 mM Tris-HCl, pH 8.0/0.5% Triton X-100/10 mM EDTA extraction; lane 5, soluble proteins in 50 mM Tris-HCl, pH 8.0/1% octylglucoside extraction; lane 6, flow-through fraction after DEAE-Sephacel column; lane 7, flow-through fraction after HTP column; lane 8, purified H91A Hin47; lane 9, purified rHia protein.

The *H. influenzae* Hia or Hsf proteins are demonstrated adhesins and as such are important vaccine candidates. The production of recombinant *H. influenzae* Hia proteins from *E. coli* has been described in the aforementioned U.S. Pat. No. 6,335,182. The full-length proteins were expressed at very low levels and were apparently toxic to *E. coli*. A series of truncated rHia proteins was made, which were sequentially deleted at the N-terminus. The V38 rHia protein was produced as "soft" inclusion bodies and was purified, as described in the aforementioned U.S. Pat. No. 6,335,182. When the V38 rHia protein was co-produced with mature H91A Hin47, its solubility was increased. This led to an improved recovery during protein purification, and represents a novel use of mature H91A Hin47 (FIG. 8). When analysed by SDS-PAGE, the V38 rHia protein was apparently produced as two doublets, whether or not it was co-produced with mature H91A Hin47 (FIG. 6).

Figure 11:
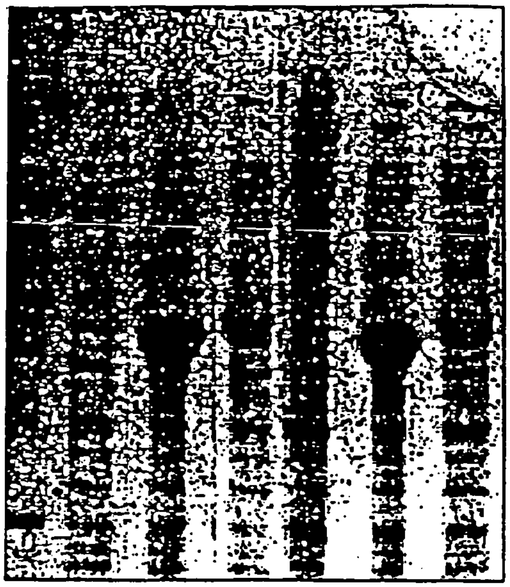
FIG. 11 contains an SDS-PAGE analysis of the production of S44 rHia and H91A Hin47±leader, when co-expressed from the same plasmid. Lane 1, H91A Hin47−leader, $t_0$; lane 2, H91A Hin47−leader, $t_4$; lane 3, H91A Hin47+leader, $t_4$; lane 4, S44 rHia, $t_4$; lane 5, H91A Hin47 (−L)+S44 rHia, $t_4$; lane 6, H91A Hin47 (+L)+S44 rHia, $t_4$.

The S44 rHia protein, prepared as described in the aforementioned PCT Patent Application No. PCT/CA00/00289 filed Mar. 16, 2000, was also produced as "soft" inclusion bodies and was purified by the same process as the V38 rHia protein. When analysed by SDS-PAGE, the S44 rHia protein was apparently produced as two doublets, if produced alone. When S44 rHia was co-produced with mature H91A Hin47, SDS-PAGE analysis revealed that it was apparently a single species (FIG. 11). This apparent stabilization of a co-produced protein represents a novel use of mature H91A Hin47.

3. Production of Recombinant *S. Pneumoniae* PsaA Protein in the Presence of *H. Influenzae* H91A Hin47.

The majority of acute bacterial otitis media is caused by *S. pneumoniae, H. influenzae* and *M catarrhalis* infections. A broadly effective vaccine against this disease would ideally include antigens from all three organisms. The production of a multi-component vaccine based upon recombinant proteins can be time-consuming and/or costly. If antigens could be co-produced, the cycle time for vaccine preparation could be reduced. In order for this to be effective, the antigens should be made in similar quantities, if they are to be combined in a 1:1 ratio in the final vaccine. It must also be possible to separate them during purification.

Figure 14:
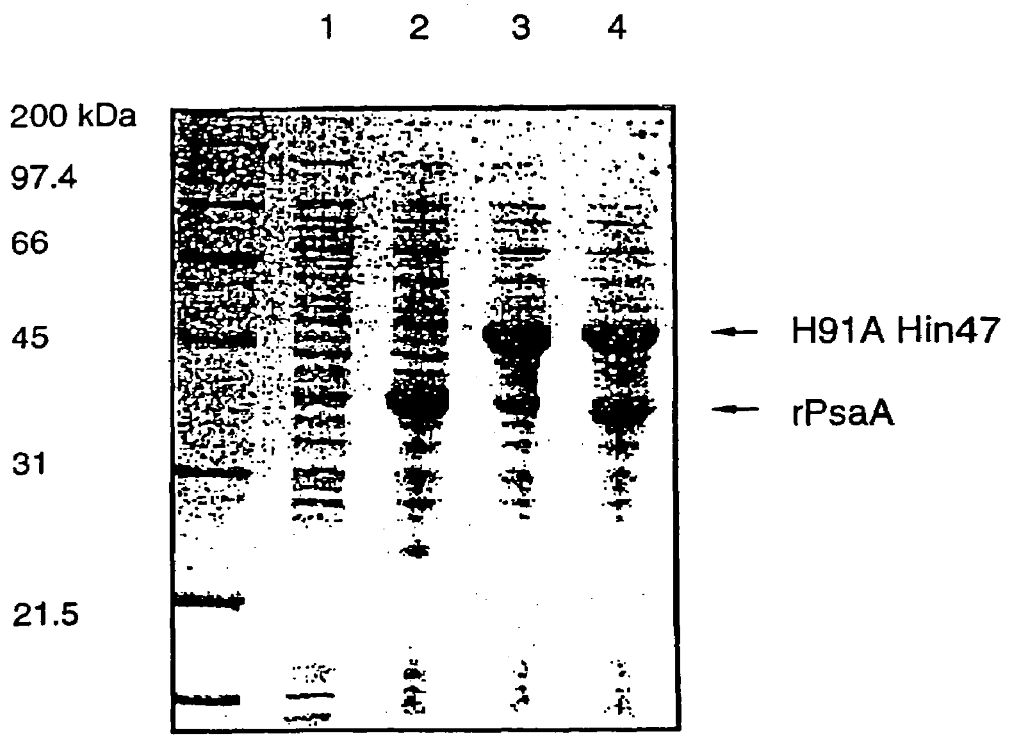
FIG. 14 contains an SDS-PAGE analysis of the production of rPsaA±leader and H91A Hin47 proteins, when co-expressed from the same plasmid. Lane 1, H91A Hin47+rPsaA (+L) at $t_0$; lane 2, H91A Hin47+rPsaA (+L) at $t_4$ (< > orientation); lane 3, H91A Hin47+rPsaA (+L) at $t_4$ (> > orientation); lane 4, H91A Hin47+rPsaA (−L) at $t_4$ (> > orientation).

The *S. pneumoniae* PsaA protein is a demonstrated adhesin that is protective in an animal model, and, as such, represents an important vaccine candidate. The native PsaA protein is a lipoprotein. The recombinant mature PsaA and lipo PsaA proteins are both made in high yield (30 to 40% of total protein) from *E. coli*. The mature protein is produced as a soluble protein and the lipoprotein appears to be membrane-associated. The recombinant mature H91A Hin47 vaccine component is also produced in high yield at 40 to 50% of total *E. coli* proteins. When the rPsaA and H91A Hin47 proteins are co-produced, they are still made in high yield, at 20 to 30% of total protein each (FIG. 14).

Figure 16:
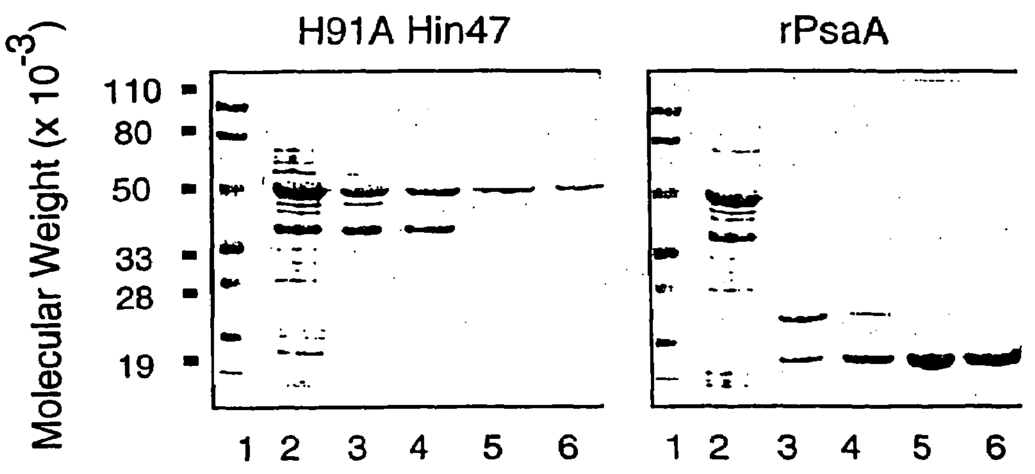
FIG. 16, having Panels A and B, contains SDS-PAGE analysis of the purification of H91A Hin47 (Panel A) and rPsaA (Panel B) (without leader). Lane 1, Prestained molecular weight markers; lane 2, *E. coli* cell lysate; lane 3, soluble proteins after 50 mM Tris-HCl, pH 8.0 extraction; lane 4, purification on DEAE-Sephacel column; lane 5, purification on HTP column; lane 6, flow-through fraction after Sartobind Q membrane, purified H91A Hin47 protein or rPsaA.

The procedure for purification of the mature rPsaA and H91A Hin47 proteins is shown in FIG. 16. Both H91A Hin47 and rPsaA (without leader) were expressed as soluble proteins. Separation of H91A Hin47 from rPsaA was achieved on a DEAE-Sephacel column, to which rPsaA bound, whereas H91A Hin47 did not. Further purification of both proteins included HTP chromatography and Sartobind Q-membrane.

4. Production of Recombinant *H. Influenzae* HMWB and/or HMWC Proteins as Potential Chaperones.

The *H. influenzae* HMWA protein is a demonstrated adhesin that is protective in animal models. The production of rHMWA proteins has been described in the aforementioned U.S. patent application Ser. No. 09/167,568. The *H. influenzae* HMWA protein is produced as a large precursor, from which a 35 kDa N-terminal fragment is cleaved during processing and secretion. The *H. influenzae* HMWA protein is encoded as part of an operon, hmwABC, that also encodes two accessory proteins termed HMWB and HMWC, that are thought to function as chaperones. The rHMWB and rHMWC proteins are made in good yield from *E. coli*, when expressed from the hmwABC operon. It has been demonstrated that the properties of a recombinant protein can be significantly altered when co-produced with the putative chaperone H91A Hin47. It would be interesting to determine what effect there would be on recombinant proteins co-produced with the *H. influenzae* rHMWB and/or rHMWC putative chaperone proteins.

It would be advantageous to express the hmwB and hmwC genes separately. Therefore, vectors have been designed to express the individual hmwB, hmwC, or hmwBC genes. Other genes encoding proteins of interest may be co-expressed with the hmwB, hmwC, or hmwBC genes.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used, but not explicitly described in this disclosure and these Examples, are amply reported in the scientific literature and are well within the ability of those skilled in the art.

Example 1

This Example describes the construction of plasmid JB-3120-2, which contains the T7 H91A hin47 gene encoding the endogenous leader sequence. The procedure employed is shown schematically in FIG. 1A.

Figure 1A:
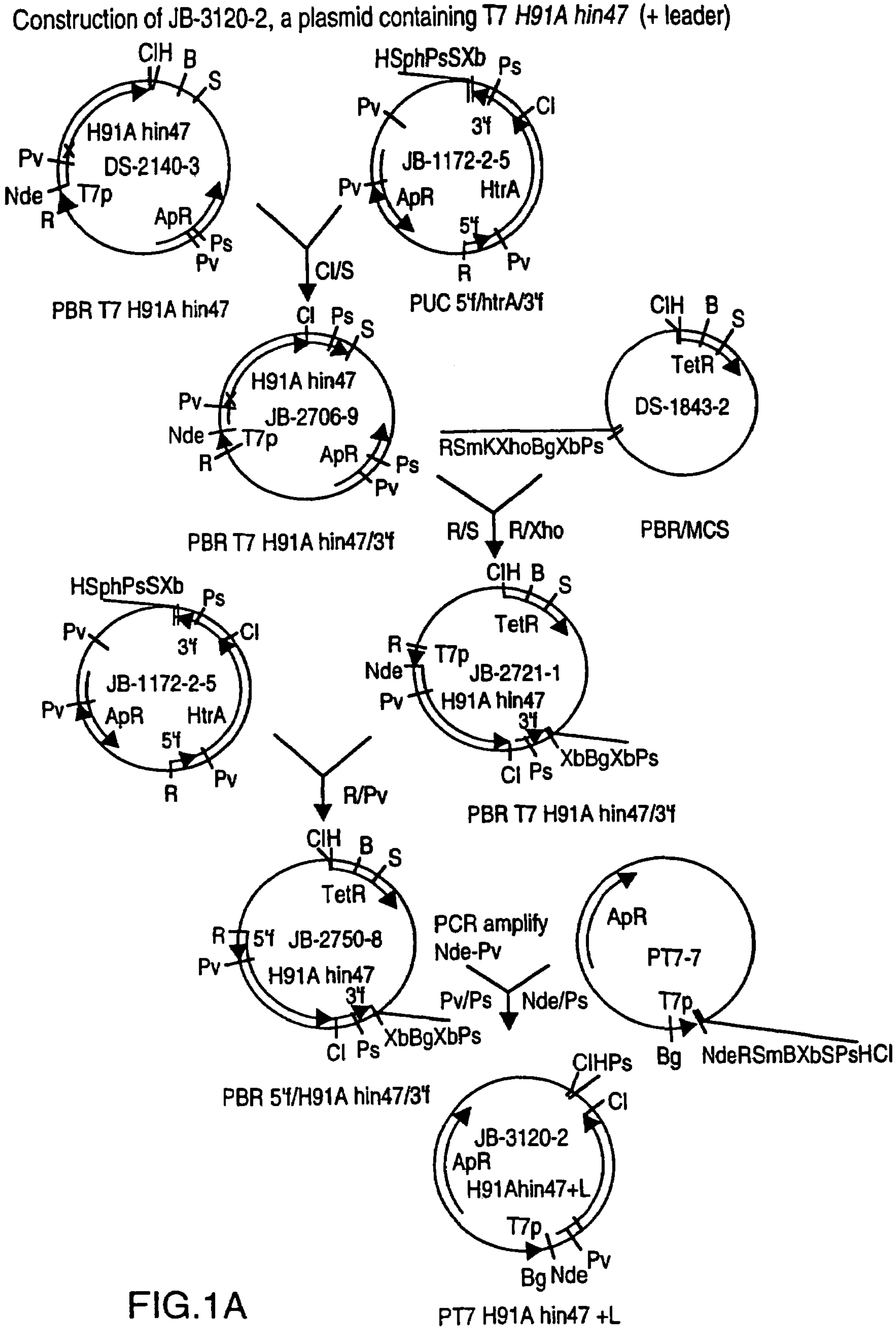
FIG. 1A describes the construction of vector JB-3120-2, a plasmid containing the H91A hin47 gene including the sequence encoding the leader sequence. Restriction sites are: B, BamH I; Bg, Bgl II; Cl, Cla I; H, Hind III; Nde, Nde I; Ps, Pst I; Pv, Pvu I; R, EcoR I; S, Sal I, Xb, Xba I; Xho, Xho I. Other abbreviations are: T7p, T7 promoter; htrA, wild-type Hin47 gene; ApR, ampicillin resistance; TetR, tetracycline resistance; 5'f, 5'-flanking sequence; 3'f, 3'-flanking sequence. The X marks the site of the H91A mutation.

The production of the mature recombinant H91A Hin47 protein from *E. coli* has been described in the aforementioned U.S. Pat. No. 5,506,139. This protein was produced at 40 to 50% of total protein in a soluble form. The bacterial HtrA proteins are located in the periplasmic membrane and may function as chaperones if located there. In order to direct the mutant, non-proteolytic H91A Hin47 protein to the periplasmic membrane, the endogenous leader was added. Plasmid DS-2140-3 is a pBR328-based plasmid that contains the T7 H91A hin47 gene cassette between EcoR I and Cla I sites (FIG. 1A). Plasmid JB-1172-2-5 is a pUC-based plasmid that contains the wild-type htrA gene with 5'- and 3'-flanking sequences. Plasmid JB-1172-2-5 was digested with Cla I and Sal I and the 0.6 kb 3'-flanking fragment was purified. Plasmid DS-2140-3 was digested with Cla I and Sal I, the 5.1 kb fragment purified, and the 3'-flanking fragment inserted, to generate plasmid JB-2706-9. Plasmid DS-1843-2 is a pBR328-based vector into which a multiple cloning site has been inserted. JB-2706-9 was digested with EcoR I and Sal I, releasing the 2.5 kb T7 H91A hin47/3'f gene sequence. The EcoR I-Sal I fragment was inserted into DS-1843-2, that had been digested with EcoR I and Xho I, generating plasmid JB-2721-1. Plasmid JB-1172-2-5 was digested with EcoR I and Pvu I to release the 0.6 kb 5'-flanking sequence. Plasmid JB-2721-1 was digested with EcoR I and Pvu I to delete the T7 promoter sequence and the 5'-flanking sequence was inserted, generating plasmid JB-2750-8, that contains a genomic 5'-flanking/htrA*/3'-flanking sequence with the H91A mutation. The HtrA leader sequence was PCR amplified from JB-2750-8 on a 0.25 kb Nde I-Pvu I fragment, using the oligonucleotide primers shown in FIG. 1B. Plasmid JB-2750-8 was digested with Pvu I and Pst I and the 1.7 kb H91A hin47/3'-flanking fragment was purified. Vector pT7-7 was digested with Nde I and Pst I and the Nde I-Pvu I and Pvu I-Pst I fragments inserted, to generate plasmid JB-3120-2. Plasmid DNA was introduced into electrocompetent *E. coli* BL21(DE3) cells using a BioRad electroporator and recombinant *E. coli* strain JB-3129-1 was grown for protein analysis, as described in the following Example.

Example 2

This Example describes the production and purification of recombinant H91A Hin47 protein with its endogenous leader sequence.

Figure 2:
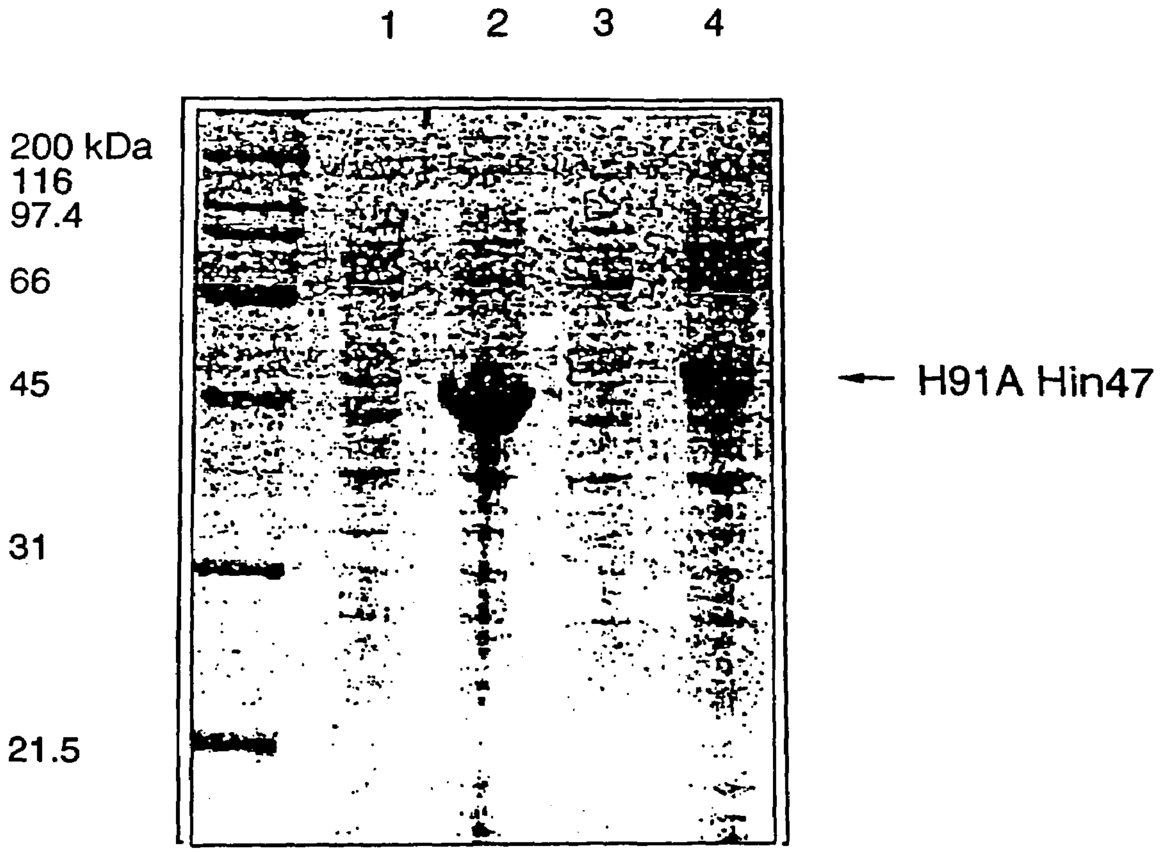
FIG. 2 contains an SDS-PAGE analysis of the production of H91A Hin47, with or without its leader sequence. Lane 1, H91A hin47−leader, $t_0$; lane 2, H91A hin47−leader, $t_4$; lane 3, H91A hin47+leader, $t_0$; H91A hin47+leader, $t_4$.
Figure 3:
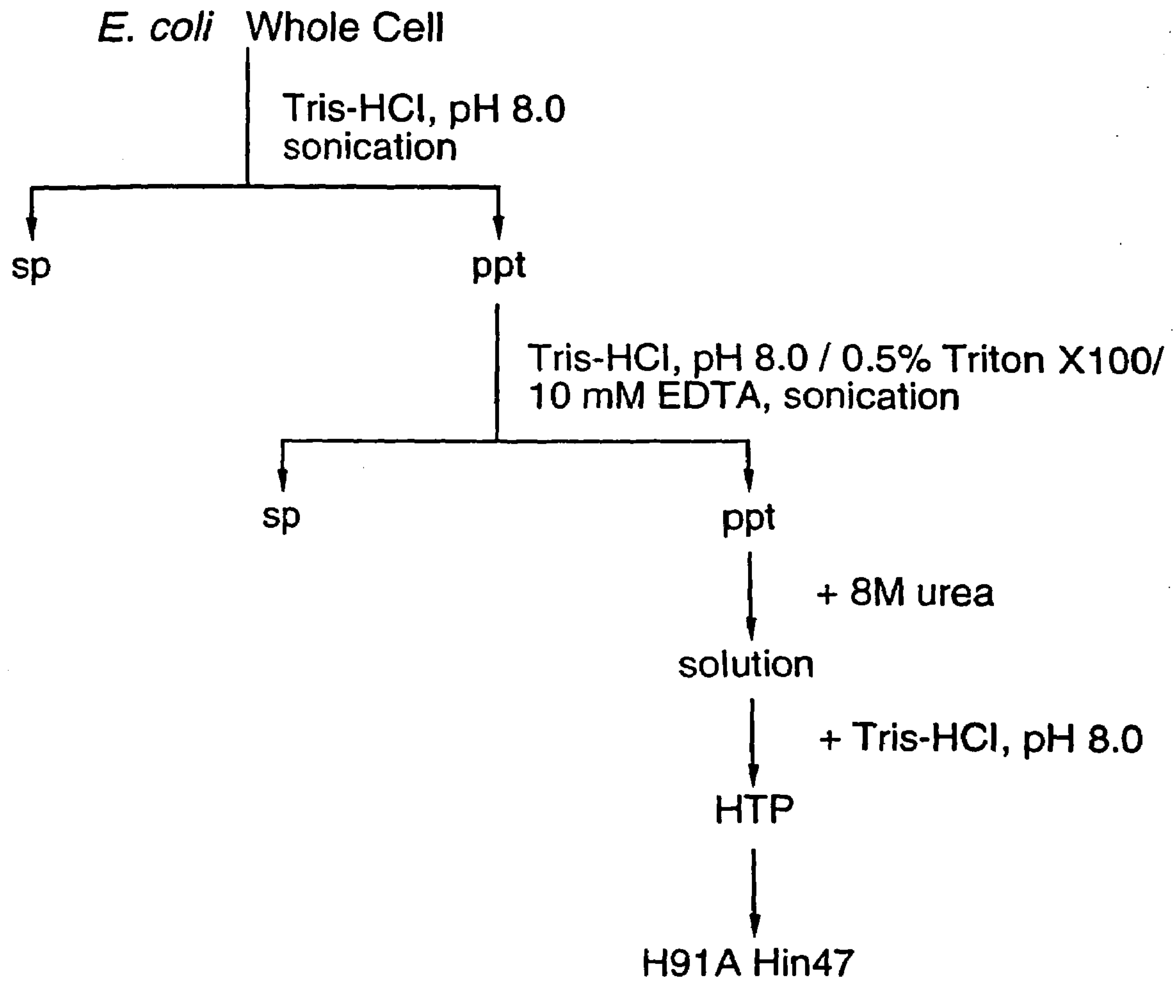
FIG. 3 shows the purification scheme for H91A Hin47 with leader.

Cells were grown at 37° C. in NZCYM medium using the appropriate antibiotic selection to $A_{578}$ of 0.3 before addition of lactose to 1.0% for 4 hours. Samples were adjusted to 0.2 OD/μl with SDS-PAGE lysis+loading buffer and the same amount of each protein sample was loaded onto SDS-PAGE gels (ref. 18). The mature H91A Hin47 protein was produced at ~50% of total protein, while the H91A Hin47+leader protein was produced at 20 to 25% of total protein (FIG. 2).

The purification of the mature soluble H91A Hin47 protein has been described in U.S. Pat. No. 5,506,139. The H91A Hin47+leader protein was found to be associated with the pellet after two extractions of *E. coli* cells with 50 mM Tris-HCl, pH 8.0 and 50 mM Tris-HCl, pH 8.0 containing 0.5% Triton X-100 and 10 mM EDTA. The pellet containing H91A Hin47 was solubilized in 50 mM Tris-HCl, pH 8.0, containing 8 M urea. After the pellets were dissolved, 50 mM Tris-HCl, pH 8.0 was added to bring the final urea concentration to 2 M.

The above solution was then applied to a Macro-prep ceramic hydroxyapatite column (HTP, Bio-Rad Laboratories) equilibrated in 10 mM Na—$PO_4$ buffer, pH 8.0. H91A Hin47 protein bound to the HTP column. After washing the column with 10 column volumes of 175 mM Na—$PO_4$, pH 8.0, H91A Hin47 was eluted from the HTP with 0.3 M Na—PO4, pH 8.0. The amount of H91A Hin47 in the elution fractions was determined by the bicinchoninic acid (BCA) protein assay using BSA as a standard. The purity of final preparation was assessed by SDS-PAGE analysis.

Example 3

This Example illustrates the construction of plasmid DS-2342-2-2, which contains the T7 H91A hin47, T7 V38 hia, and *E. coli* cer genes. The procedure employed is shown schematically in FIG. 5.

Figure 5:
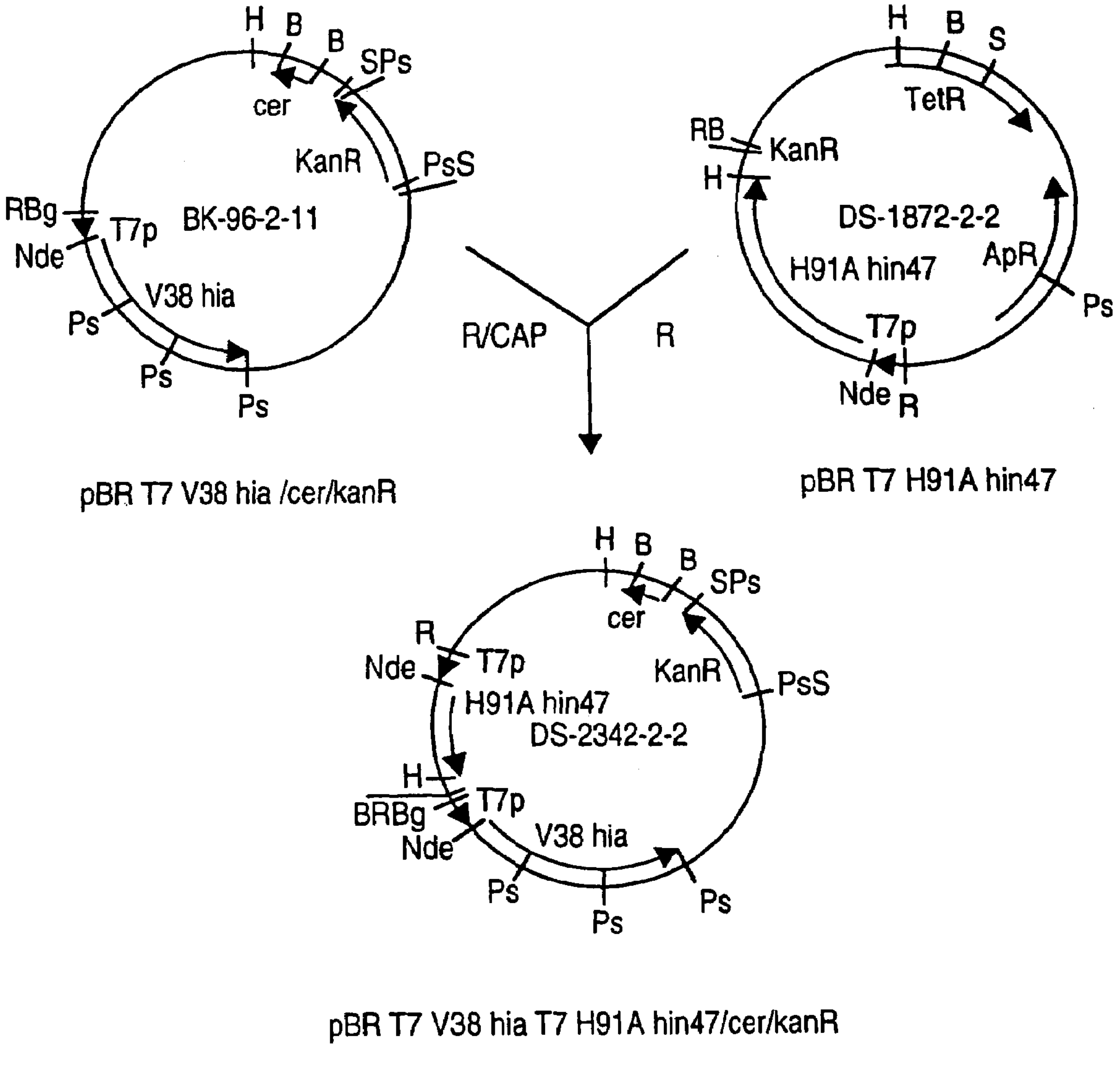
FIG. 5 shows the construction of vector DS-2342-2-2, a plasmid containing the T7 H91A hin47 and T7 V38 hia gene cassettes. The H91A hin47 gene encodes the mature protein. Restriction sites are: B, BamH I; Bg, Bgl II; H, Hind III; Nde, Nde I; Ps, Pst I; R, EcoR I; S, Sal I. Other abbreviations are: CAP, calf alkaline phosphatase; T7p, T7 promoter; ApR, ampicillin resistance; KanR, kanamycin resistance; TetR, tetracycline resistance.

Plasmid DS-1872-2-2 is a pBR328-based vector containing a 2.2 kb EcoR I T7 H91A hin47 gene cassette (FIG. 5). Plasmid BK-96-2-11 is a pBR328-based vector that contains a T7 V38 hia gene cassette, the *E. coli* cer gene, and a kanamycin resistance gene; and this plasmid has been described in the aforementioned U.S. Pat. No. 6,335,182. BK-96-2-11 was linearized by digestion with EcoR I, dephosphorylated, and the EcoR I T7 H91A hin47 gene fragment inserted, to generate plasmid DS-2342-2-2, that co-expresses the H91A hin47 and V38 hia genes. This plasmid thus contains tandem T7 H91A hin47 and T7 V38 hia genes in the same orientation. Plasmid DNA was introduced into electrocompetent *E. coli* BL21 (DE3) cells using a BioRad electroporator, and recombinant *E. coli* strain DS-2350-3-1 was grown for protein analysis, as described in the following Example.

Example 4

This Example describes the production and purification of recombinant V38 rHia protein that was co-produced with H91A Hin47.

Protein samples were prepared and analysed as described in Example 2. The V38 rHia and mature H91A Hin47 proteins were both produced upon induction (FIG. 6). The V38 rHia protein appeared as a pair of doublets on SDS-PAGE, whether or not it was produced in the presence of H91A Hin47.

Figure 7:
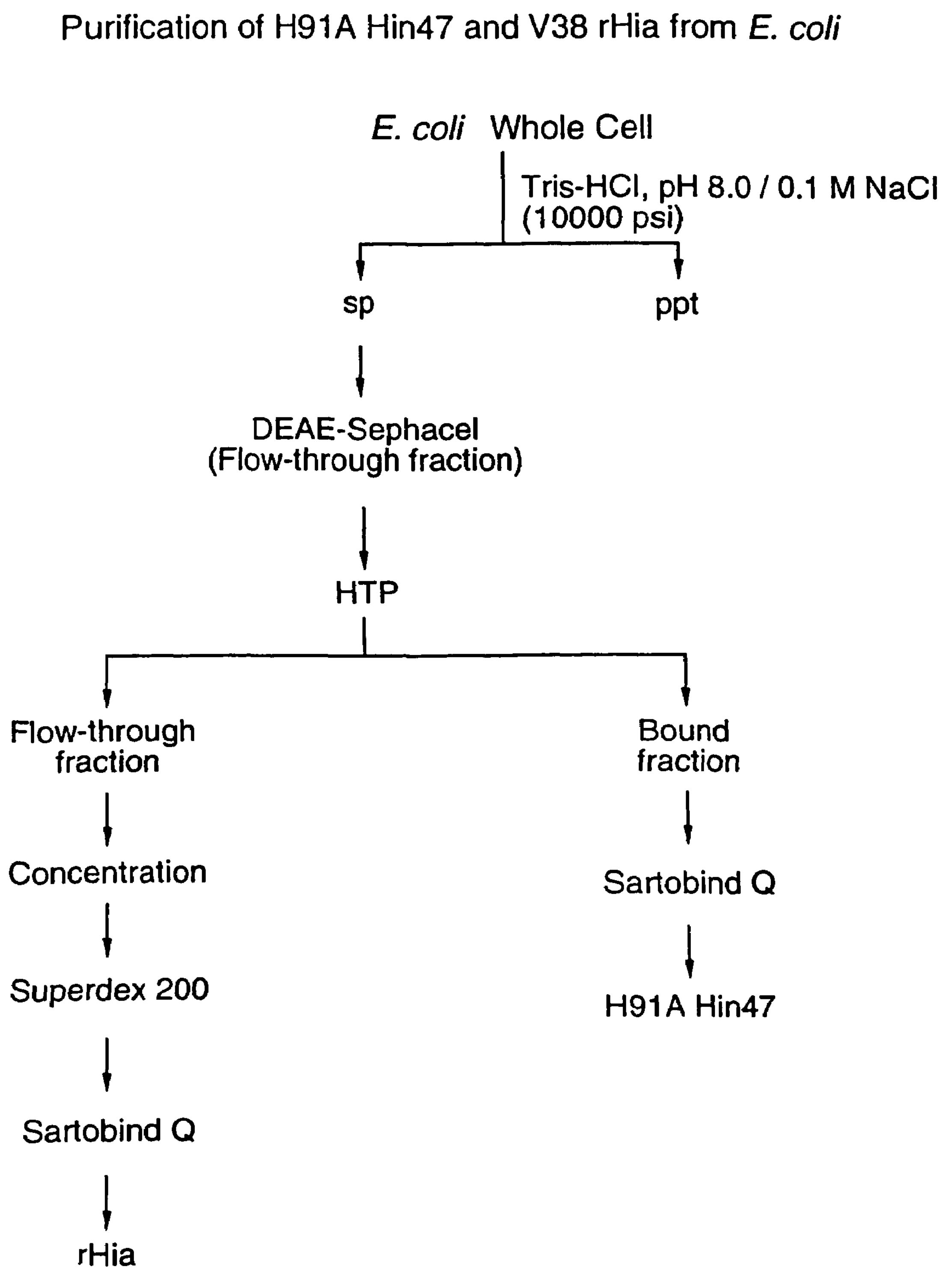
FIG. 7 shows the purification scheme for V38 rHia when co-expressed with H91A Hin47.

The purification of V38 rHia, produced as inclusion bodies, has been described in U.S. patent application Ser. No. 09/268,347. When co-produced with H91A Hin47, the V38 rHia protein was apparently more soluble; and the majority of rHia protein was recovered in the initial 50 mM Tris-HCl, pH 8.0/0.1 M NaCl extraction. As shown in FIGS. 7 and 8, the separation of rHia from H91A Hin47 was achieved through a HTP column, to which H91A Hin47 protein bound but rHia did not. After concentration of rHia by PEG 4000 or ammonium sulfate, the protein was further purified on a Superdex 200 gel filtration column, the same process used for the purification of rHia expressed as inclusion bodies. A Sartibond Q membrane was used as a final polishing step to further remove LPS and residual contaminants. The purity of rHia or H91A Hin47 was assessed by SDS-PAGE analysis (FIG. 8), according to the procedure of Laemmli (ref 18).

Example 5

This Example illustrates the construction of plasmid JB-3134-1-1, which contains the T7 S44 hia and T7 H91A hin47 (no leader) genes. The procedure employed is shown schematically in FIG. 9.

Figure 9:
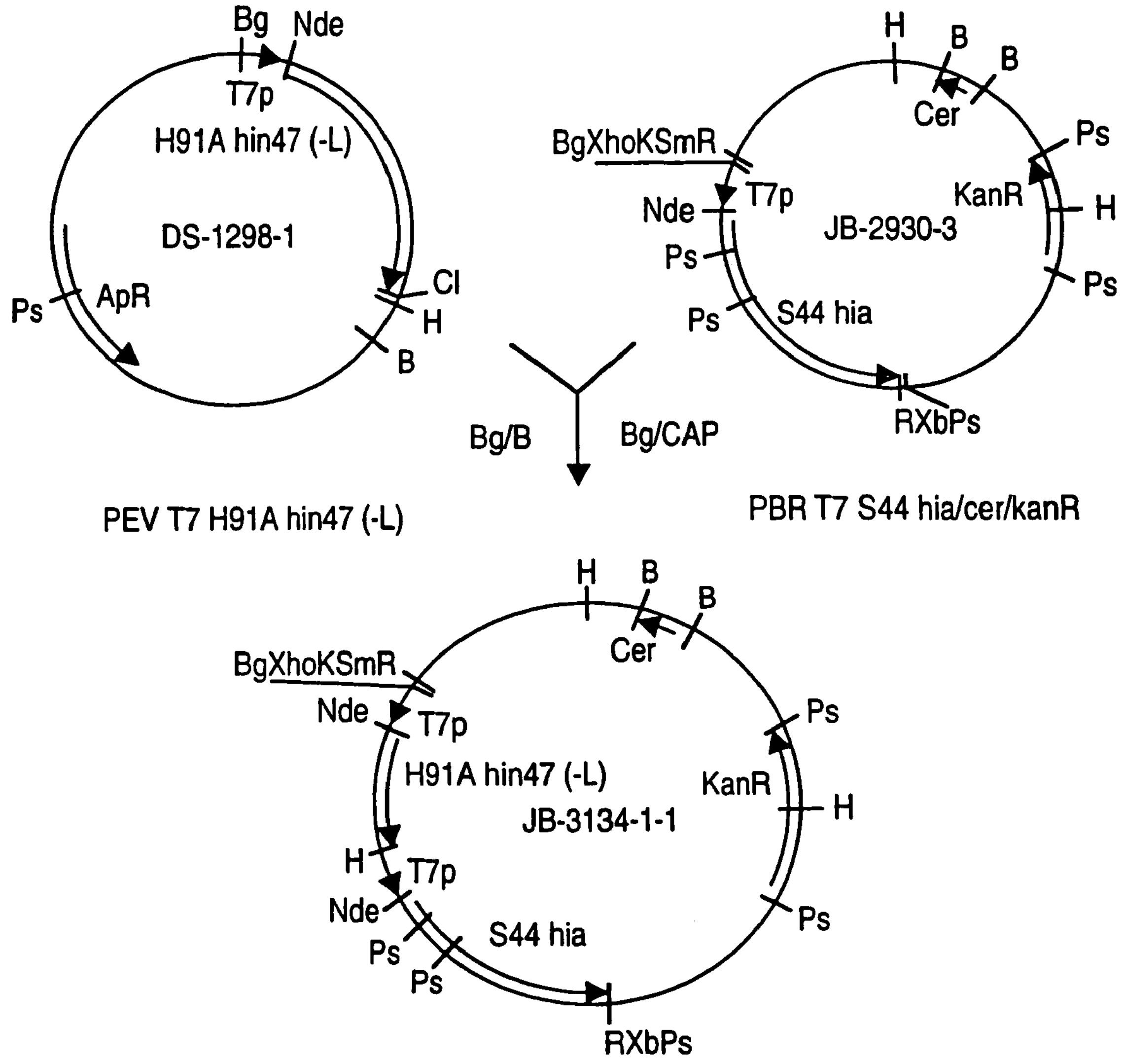
FIG. 9 shows the construction of vector JB-3134-1-1, a plasmid containing the T7 H91A hin47 and T7 S44 hia gene cassettes. The H91A hin47 gene encodes the mature protein. Restriction sites are: B, BamH I; Bg, Bgl II; Cl, Cla I; H, Hind III; Nde, Nde I; Ps, Pst I; R, EcoR I. Other abbreviations are: CAP, calf alkaline phosphatase; T7p, T7 promoter; ApR, ampicillin resistance; KanR, kanamycin resistance.

Plasmid DS-1298-1 is a pBR322-based plasmid (pEV, ref. 19) that contains the T7 H91A hin47 gene on a 2.2 kb Bgl II-BamH I fragment (FIG. 9). Plasmid JB-2930-3 is a pBR328-based vector that contains the T7 S44 hia, *E. coli* cer, and kanamycin resistance genes and is described in the aforementioned PCT Patent Application No. PCT/CA00/00289. Plasmid JB-2930-3 was linearized by digestion with Bgl II, dephosphorylated, and the Bgl II-BamH I T7 H91A hin47 gene fragment inserted to generate plasmid JB-3134-1-1. This plasmid thus contains tandem T7 H91A hin47 (−L) and T7 S44 hia genes in the same orientation. Plasmid DNA was introduced into electrocompetent *E. coli* BL21(DE3) cells using a BioRad electroporator, and recombinant *E. coli* strain JB-3144-1 was grown for protein analysis.

Example 6

This Example illustrates the construction of plasmid JB-3145-1, which contains the T7 S44 hia and T7 H91A hin47 (with leader) genes. The procedure employed is shown schematically in FIG. 10.

Figure 10:
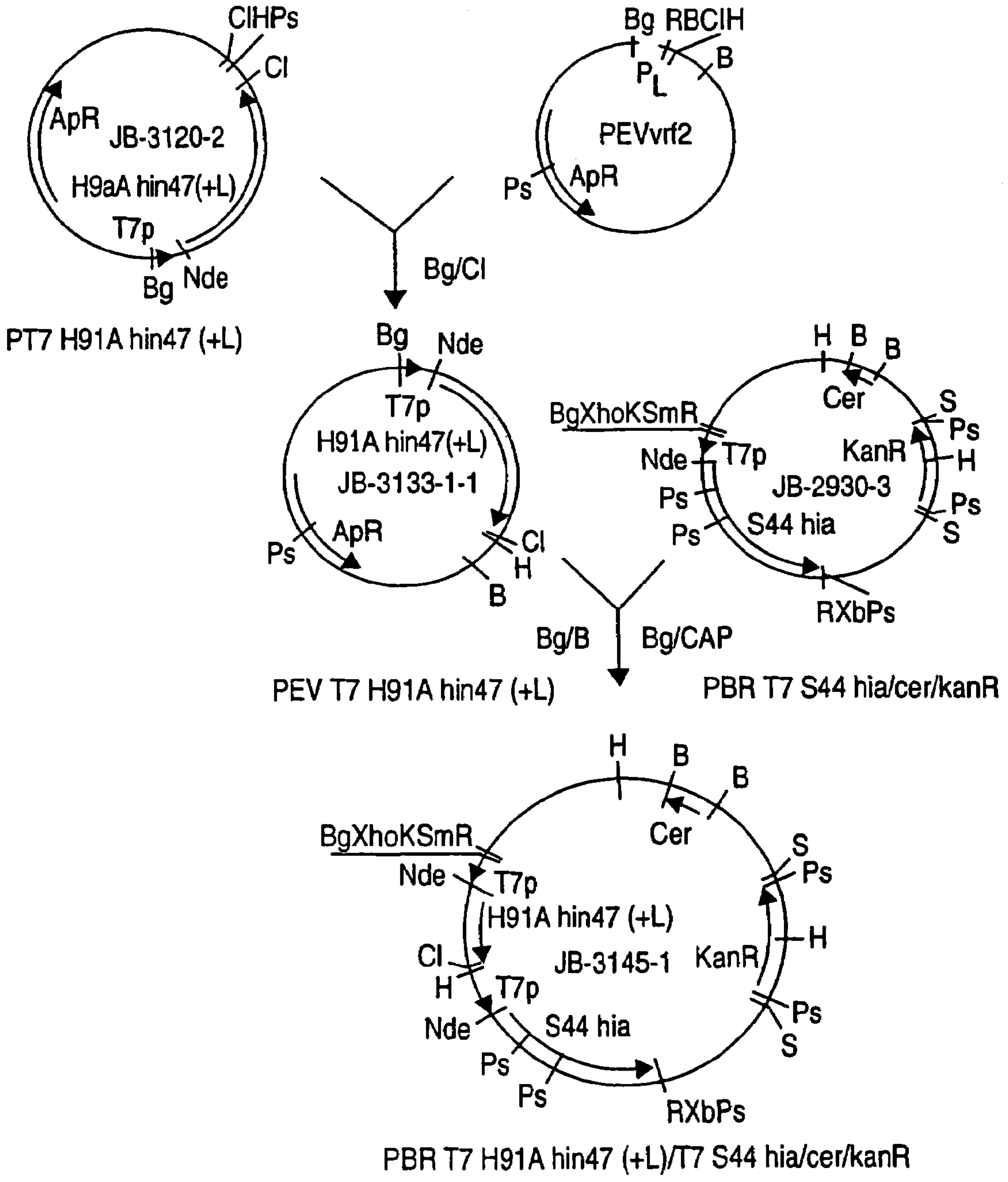
FIG. 10 shows the construction of vector JB-3145-1, a plasmid containing the t7 H91A hin47 and T7 S44 hia gene cassettes. The H91A hin47 gene encodes the protein with its leader sequence. Restriction sites are: B, BamH; Bg, Bgl II; Cl, Cla I; H, Hind III; Nde, Nde I; Ps, Pst I; R, EcoR I. Other abbreviations are: CAP, calf alkaline phosphatase; T7p, T7 promoter; ApR, ampicillin resistance; KanR, kanamycin resistance.

Plasmid JB-3120-2, prepared as described in Example 1, contains the T7 H91A hin47 (+leader) cassette on a Bgl II-Cla I fragment (FIG. 10). Plasmid pEVvrf2 is a pBR322-based plasmid containing the $\gamma P_L$ promoter and a multiple cloning site (ref 19). Plasmid pEVvrf2 was digested with Bgl II and Cla I, and the T7 H91A hin47 (+L) gene cassette was inserted to generate plasmid JB-3133-1-1. This plasmid contains the T7 H91A hin47 (+L) gene cassette on a Bgl II-BamH I fragment. Plasmid JB-2930-3 is a pBR328-based vector that contains the T7 S44 hia, *E. coli* cer, and kanamycin resistance genes, and is prepared as described in the aforementioned PCT Patent Application No. PCT/CA00/00289. Plasmid JB-2930-3 was digested with Bgl II, dephosphorylated, and the Bgl II-BamH I T7 H91A hin47 (+L) fragment was inserted to generate plasmid JB-3145-1. This plasmid thus contains tandem T7 H91A hin47 (+L) and T7 S44 hia genes in the same orientation. Plasmid DNA was introduced into electrocompetent *E. coli* BL21(DE3) cells using a BioRad electroporator and recombinant *E. coli* strain JB-3153-1-1 was grown for protein analysis.

Example 7

This Example describes the production of recombinant S44 rHia protein that was co-produced with H91A Hin47±leader.

Protein samples, produced by the plasmids JB-3134-1-1 and JB-3145-1, described in Examples 5 and 6, were prepared and analysed as described in Example 2. The S44 rHia and mature H91A Hin47, proteins were both produced upon induction (FIG. 11). The S44 rHia protein appeared as a pair of doublets when expressed alone, but as a single band when co-expressed with H91A Hin47 (−L). The H91A Hin47 protein appears to have enhanced the stability of the co-produced S44 rHia protein. The S44 rHia and H91A Hin47 (with leader) proteins were both produced upon induction, although the amount of S44 rHia was significantly reduced (FIG. 11).

Example 8

This Example describes the construction of plasmid JB-3073R-1, which contains the T7 H91A hin47 and T7 psaA (with leader) genes. The procedure employed is shown schematically in FIG. 12A.

Figure 12A:
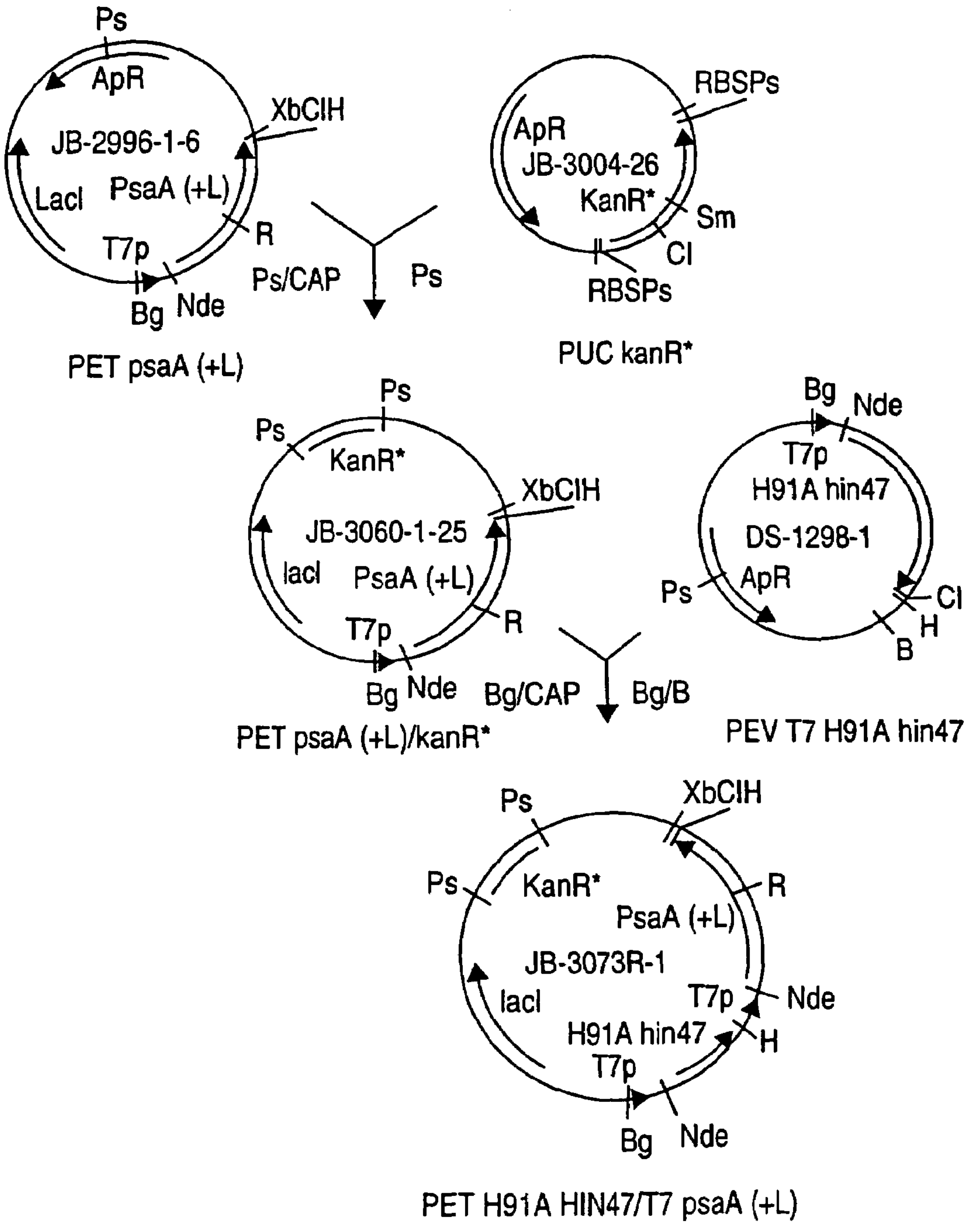
FIG. 12A shows the construction of vector JB-3073R-1, a plasmid containing the T7 psaA and T7 H91A hin47 gene cassettes. The psaA gene encodes its endogenous leader sequence. Restriction sites are: B, BamH I; Bg, Bgl II; Cl, Cla I; H, Hind III; Nde, Nde I; Ps, Pst I; R, EcoR I, Xb, Xba I. Other abbreviations are: CAP, calf alkaline phosphatase; T7p, T7 promoter; ApR, ampicillin resistance; KanR*, kanamycin resistance gene with internal Hind III and Xho I sites deleted.

The *H. influenzae* H91A Hin47 and *S. pneumoniae* rPsaA proteins are both potential vaccine candidates and are made in high yield from *E. coli* when expressed individually. The production time for these vaccine antigens can be significantly reduced if they could be co-expressed and separated by purification. Plasmid JB-2996-1-6 is an ampicillin resistant pET-based vector containing a T7 psaA (+leader) gene cassette encoding the 37 kDa lipo rPsaA protein (FIG. 12A). PCR primers for amplification of the psaA(+leader) gene are described in FIG. 12B. Plasmid JB-3004-26 was derived from plasmid pUC-4K (Pharmacia) by site-directed mutagenesis of the kanamycin resistance (kanR) gene. The interior Hind III and Xho I sites were deleted, but the Cla I and Sma I sites were unchanged. Plasmid JB-2996-1-6 was linearized with Pst I, dephosphorylated, and the mutated kanR gene from JB-3004-26 was inserted to generate JB-3060-1-25. Plasmid DS-1298-1 is a pBR322-based plasmid containing the T7 H91A hin47 gene, encoding the mature H91A Hin47 protein, on a 2.2 kb Bgl II-BamH I fragment. Plasmid JB-3060-1-25 was linearized with Bgl II, dephosphorylated, and the Bgl II-BamH I T7 H91A hin47 gene inserted to generate JB-3073R-1. This plasmid thus contains tandem T7 H91A hin47 and T7 psaA (+L) genes in the same orientation. Plasmid DNA was introduced into electrocompetent *E. coli* BL21(DE3) cells using a BioRad electroporator, and recombinant *E. coli* strain IA-181-1 was grown for protein analysis.

Example 9

This Example describes the construction of plasmids JB-3090-1 and JB-3090-7, which contain the T7 H91A hin47 and T7 psaA (no leader) genes. The procedure employed is shown schematically in FIG. 13A.

Figure 13A:
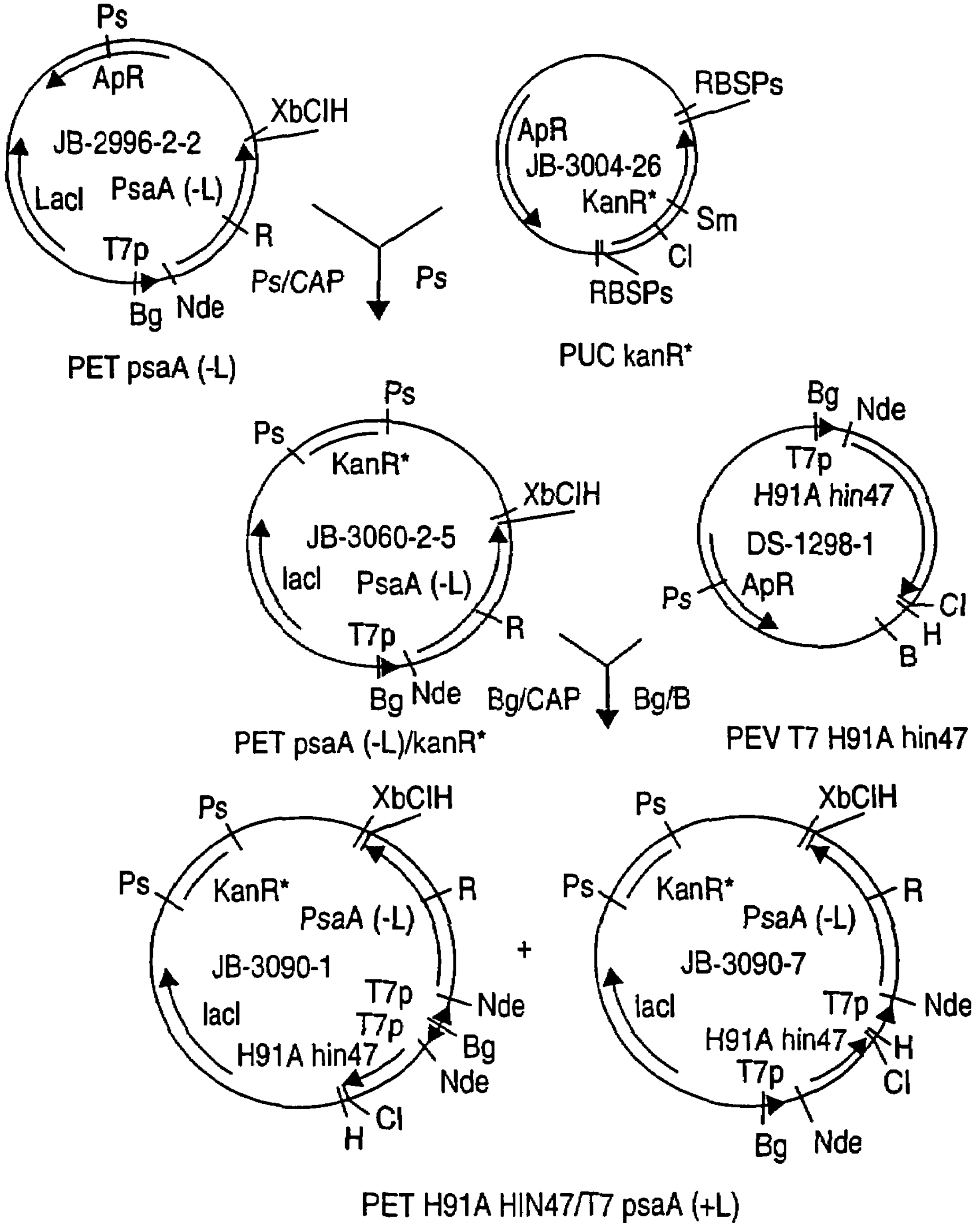
FIG. 13A shows the construction of vectors JB-3090-1 and JB-3090-7, plasmids containing the T7 psaA and T7 H91A hin47 gene cassettes, in different orientations. The psaA gene encodes the mature protein. Restriction sites are: B, BamH I; Bg, Bgl II; Cl, Cla I; H, Hind III; Nde, Nde I; Ps, Pst I; R, EcoR I, Xb, Xba I. Other abbreviations are: CAP, calf alkaline phosphatase; T7p, T7 promoter; ApR, ampicillin resistance; KanR*, kanamycin resistance gene with internal Hind III and Xho I sites deleted.

Plasmid JB-2996-2-2 is an ampicillin resistant pET-based vector containing a T7 psaA (−leader) gene cassette, encoding the mature rPsaA protein (FIG. 13A). PCR primers to amplify psaA (−leader) gene are described in FIG. 13B. Plasmid JB-3004-26 contains the mutated kanamycin resistance gene, as described in Example 8. Plasmid JB-2996-2-2 was linearized with Pst I, dephosphorylated, and the mutated kanR gene from JB-3004-26 was inserted to generate JB-3060-2-5. Plasmid DS-1298-1 is a pBR322-based plasmid containing the T7 H91A hin47 gene encoding the mature H91A Hin47 protein on a 2.2 kb Bgl II-BamH I fragment. Plasmid JB-3060-2-5 was linearized with Bgl II, dephosphorylated, and the Bgl II-BamH I T7 H91A hin47 gene inserted to generate plasmids JB-3090-1 and JB-3090-7. These plasmids differ only in the relative orientation of the inserted T7 H91A hin47 gene. Plasmid JB-3090-7 thus contains tandem T7 H91A hin47 and T7 psaA (−L) genes in the same orientation, while plasmid JB-3090-1 contains tandem T7 H91A hin47 and T7 psaA (−L) genes in opposite orientations. It has been noted that the latter arrangement of genes is very rarely cloned. Plasmid DNA was introduced into electrocompetent *E. coli* BL21 (DE3) cells using a BioRad electroporator; and recombinant *E. coli* strains JB-3106-1-1 (from JB-3090-1) and JB-3106-2-1 (from JB-3090-7) were grown for protein analysis.

Example 10

This Example describes the production and purification of recombinant H91A Hin47 and PsaA±leader when co-produced from the same plasmid.

Protein samples, produced by plasmids JB-3073R-1, plasmid JB-3090-1 and plasmid JB-3090-7, described in Examples 8 and 9, were prepared and analysed as described in Example 2. The rPsaA protein was produced in good yield from all strains, with or without its leader sequence (FIG. 14). However, the H91A Hin47 protein was produced from only two of three strains. When the tandem genes were arranged in the same orientation, both rPsaA and H91A Hin47 were produced in high yield. Strain JB-3106-1-1, generated from plasmid JB-3090-1 that contains the tandem genes in opposite orientations, did not produce any H91A Hin47.

Figure 15:
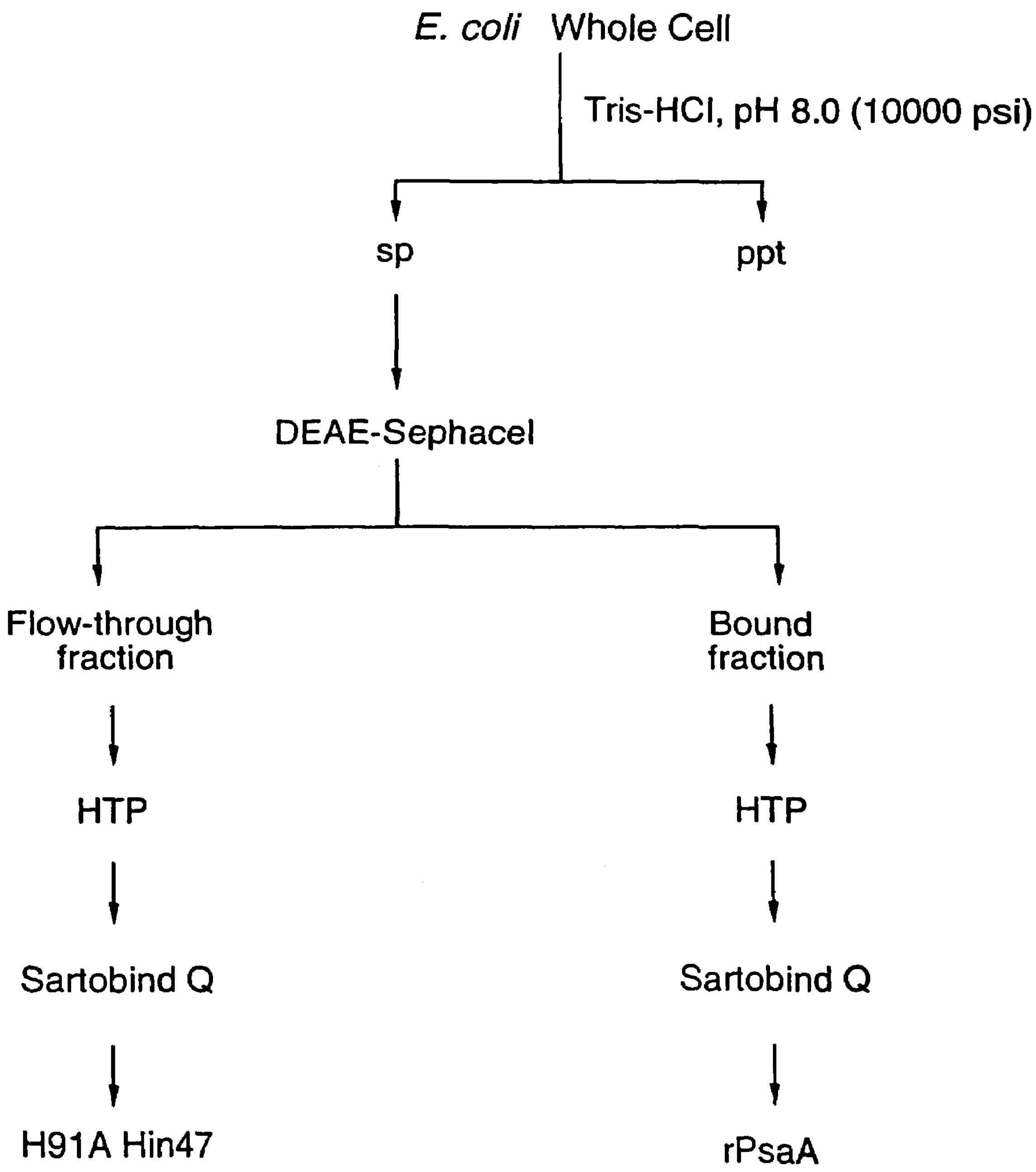
FIG. 15 shows the purification scheme for H91A Hin47 and rPsaA (without leader), when co-produced.

The scheme for separation and purification of the H91A Hin47 and rPsaA proteins is shown in FIG. 15. Both H91A Hin47 and rPsaA (without leader) were expressed as soluble proteins. After extraction with 50 mM Tris-HCl, pH 8.0, the soluble sonicate fraction was applied to a DEAE-Sephacel column equilibrated in 50 mM Tris-HCl, pH 8.0. The majority of H91A Hin47 did not bind to the column and was recovered in the flow-through fraction. In contrast, the majority of rPsaA bound to the DEAE-Sephacel. After washing with 10 column volumes of 50 mM Tris-HCl, pH 8.0/10 mM NaCl to remove contaminants, rPsaA was eluted in 50 mM Tris-HCl, pH 8.0 containing 30 mM NaCl. The H91A Hin47 or rPsaA fraction was further purified separately onto a Macro-prep ceramic hydroxylapatite column (HTP) equilibrated in 10 mM Na—PO4 buffer, pH 8.0. Both proteins bound to the HTP column. For the purification of H91A Hin47, the HTP column was washed with 10 column volumes of 175 mM Na—PO4, pH 8.0, and H91A Hin47 was eluted with 0.3 M Na—PO4, pH 8.0. For the purification of rPsaA, the HTP column was washed with 10 column volumes of 50 mM Na—PO4, pH 8.0, and rPsaA was eluted with 0.2 M Na—PO4, pH 8.0. The purity of H91A Hin47 or rPsaA was assessed by SDS-PAGE analysis (FIG. 16).

Example 11

Figure 17A:
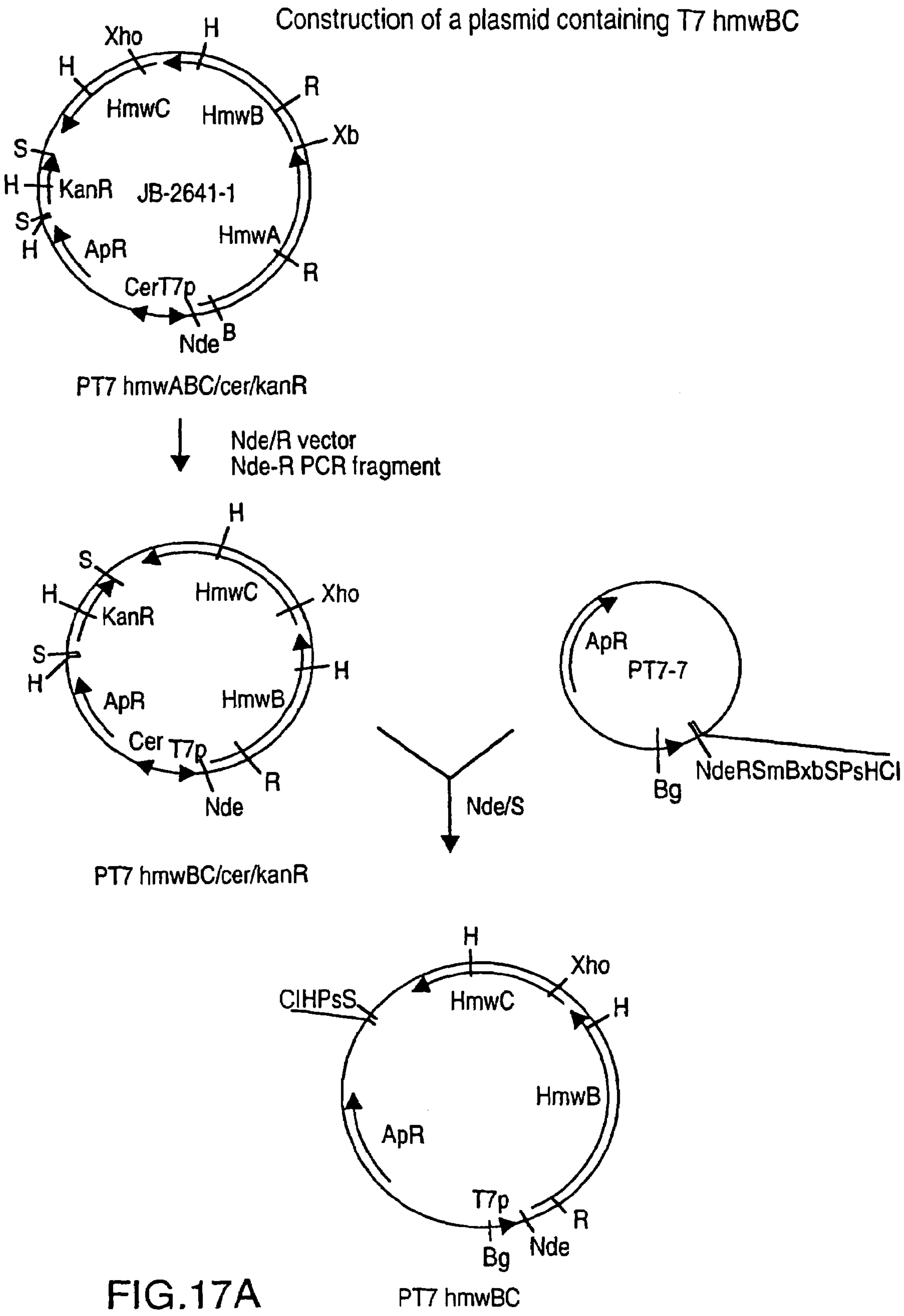
FIG. 17A describes the construction of IN-52-1-13 that co-expresses the *H. influenzae* hmwB and hmwC genes. Restriction sites are: B, BamH I; Bg, Bgl II; H, Hind III; Nde, Nde I; Ps, Pst I; R, EcoR I; S, Sal I; Xba, Xba I; Xho, Xho I. Other abbreviations are: T7p, T7 promoter; ApR, ampicillin resistance; KanR, kanamycin resistance.

This Example describes the construction of plasmid IN-52-1-13 that co-expresses *H. influenzae* hmwB and hmwC genes. The procedure employed is shown schematically in FIG. 17A.

Plasmid JB-2641-1 is a pT7-based plasmid that contains the hmwABC genes with an Xba I site inserted at the 3'-end of hmwA (FIG. 17A) and has been described in the aforementioned U.S. patent application Ser. No. 09/167,568. Digestion with Nde I and EcoR I deletes a 610 bp fragment containing the hmwA gene and the 5'-end of the hmwB gene. The 5'-end of hmwB is created by PCR amplification that also introduces an Nde I site encoding a start Met, using the oligonucleotide primers shown in FIG. 17B. The 460 bp Nde I-EcoR I PCR fragment is inserted into the Nde I-EcoR I vector to generate pT7 hmwBC/cer/kanR (IN-47-1). In order to introduce additional restriction enzyme sites for future constructions, the Nde I-Sal I fragment containing the complete T7 hmwBC gene cassette is inserted into pT7-7 to generate pT7 hmwBC (IN-52-1-13).

Example 12

This Example describes the construction of plasmid IN-137-1-16 that expresses *H. influenzae* hmwB alone. The procedure employed is shown schematically in FIG. 18A.

Figure 18A:
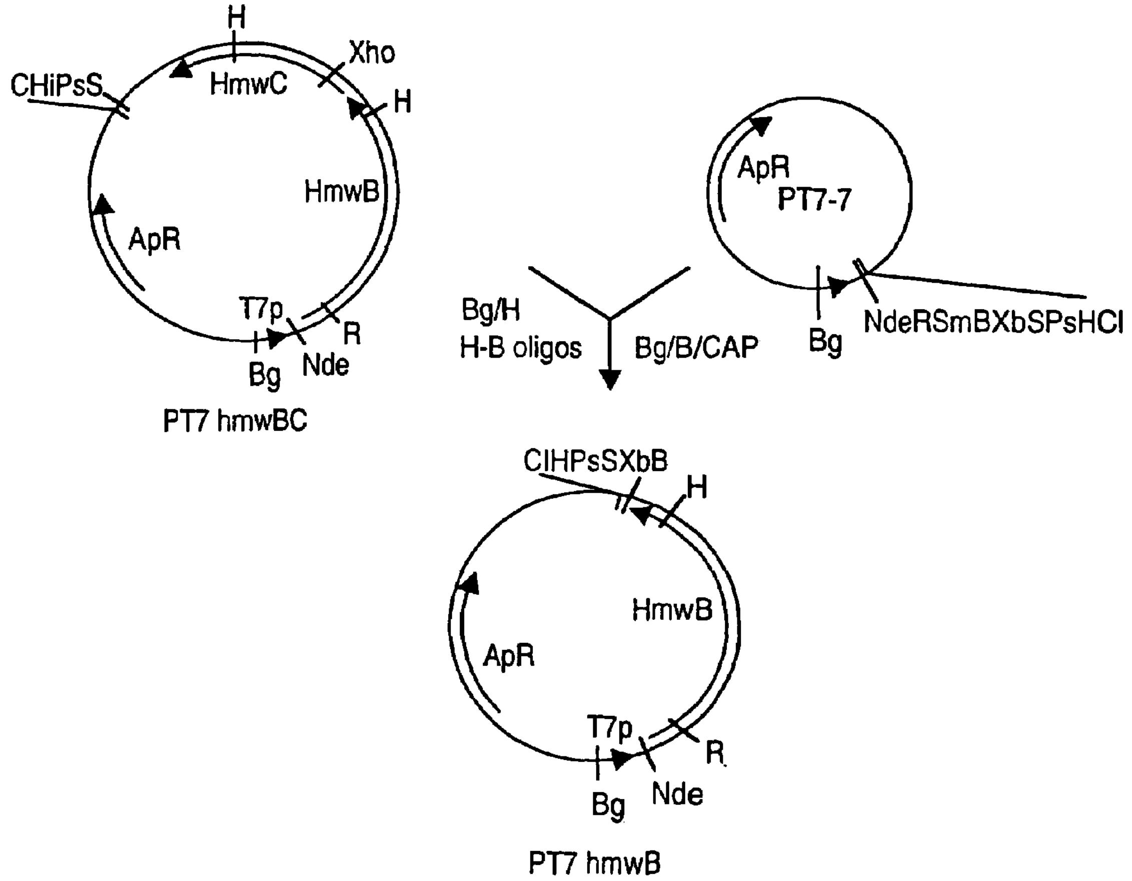
FIG. 18A shows the construction of IN-137-1-16 to express the *H. influenzae* hmwB gene alone. Restriction sites are: B, BamH I; Bg, Bgl II; Cl, Cla I; H, Hind III; Nde, Nde I; Ps, Pst I; R, EcoR I, Xho, Xho I. Other abbreviations are: CAP, calf alkaline phosphatase; T7p, T7 promoter; ApR, ampicillin resistance.

The construction of plasmid pT7 hmwBC (IN-52-1-13) is described in Example 11. Digestion of plasmid IN-52-1-13 with Bgl II and Hind III generates a fragment containing the T7 promoter and most of the hmwB gene (FIG. 18A). The 3'-end of hmwB is synthesized as a ~123 bp Hind III-BamH I fragment, using the oligonucleotides shown in FIG. 18B. The Bgl II-Hind III and Hind III-BamH I fragments are inserted into pT7-7 that has been digested with Bgl II and BamH I, then dephosphorylated. The resultant plasmid, pT7 hmwB (IN-137-1-16), contains the T7 promoter and the full-length hmwB gene only, as a Bgl II-BamH I cassette that can be used for co-expression studies.

Example 13

This Example describes the construction of a plasmid to express *H. influenzae* hmwC alone. The procedure employed is shown schematically in FIG. 19A.

Figure 19A:
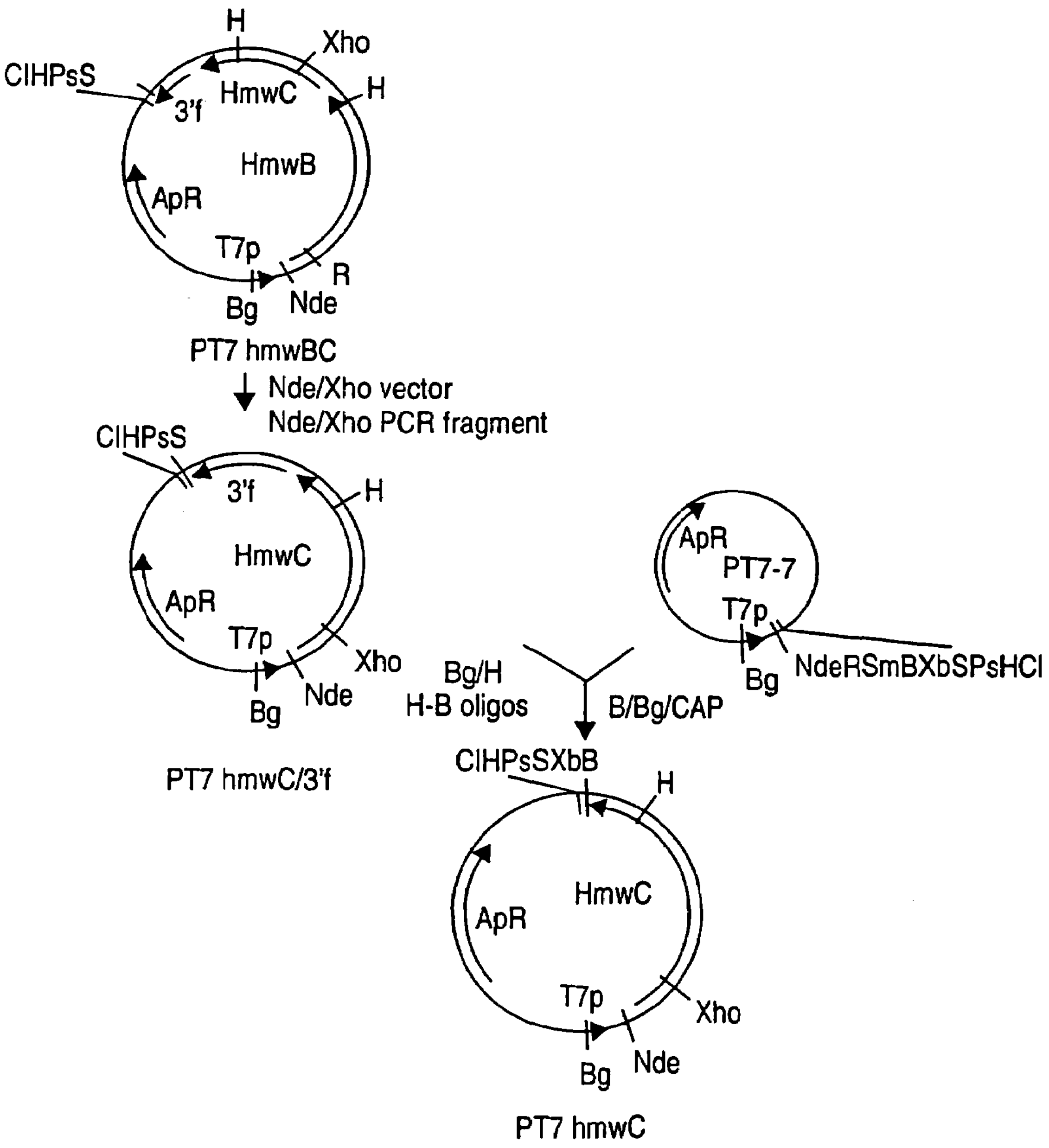
FIG. 19A shows the construction of a plasmid to express the *H. influenzae* hmwC gene. Restriction sites are: B, BamH I; Bg, Bgl II; Cl, Cla I; H, Hind III; Nde, Nde I; Ps, Pst I; R, EcoR I; Xho, Xho I. Other abbreviations are: CAP, calf alkaline phosphatase; T7p, T7 promoter; ApR, ampicillin resistance.

The construction of plasmid pT7 hmwBC (IN-52-1-13) was described in Example 11. This vector contains the complete hmwB and hmwC genes, as well as ~1.3 kb of 3'-flanking sequence. Digestion of IN-52-1-13 with Nde I and Xho I deletes the hmwB gene and the 5'-end of hmwC gene (FIG. 19A). The 5'-end of hmwC is created by PCR amplification that also introduces an Nde I site encoding a start Met. The oligonucleotide primers employed are shown in FIG. 19B. The 950 bp Nde I-Xho I 5' hmwC PCR fragment is inserted into the Nde I-Xho I vector to generate pT7 hmwC/3'f (IN-109-1). In order to create a plasmid containing only the hmwC gene with no 3'-flanking sequence, IN-109-1 was digested with Bgl II and Hind III and the ~2.2 kb fragment containing the T7 promoter and most of the hmwC gene was purified. The 3'-end of the hmwC gene is synthesized as a 80 bp Hind III-BamH I fragment from the oligonucleotides shown in FIG. 19C. The Bgl II-Hind III and Hind III-BamH I fragments are inserted into pT7-7 that has been digested with Bgl II and BamH I and dephosphorylated. The resultant plasmid, pT7 hmwC, contains the T7 promoter and the full-length hmwC gene only as a Bgl II-BamH I cassette that can be used for co-expression studies.

SUMMARY OF THE DISCLOSURE

In summary of this disclosure, there is provided a heterologous chaperone effect in the expression of recombinant proteins. Modifications are possible within the scope of the invention.

We claim:

1. An expression vector for expression of a recombinant protein in a host cell, comprising:

a nucleic acid molecule encoding a non-proteolytic mutant of a *Haemophilus* Hin47 protein wherein said Hin47 protein is mutated at amino acid 91, 121 or 197 and said nucleic acid molecule includes a portion encoding the leader sequence for said non-proteolytic mutant, at least one additional nucleic acid molecule encoding the recombinant protein, wherein the recombinant protein is a Hia protein of a strain of *Haemophilus influenzae* which is N-terminally truncated, and at least one regulatory element operatively connected to said first nucleic acid molecule and at least one regulatory element operatively connected to said at least one additional nucleic acid molecule to effect expression of at least said recombinant protein in the host cell.

2. The vector of claim 1 wherein histidine 91 is replaced by alanine.

3. The vector of claim 2, wherein said N-terminal truncation is V38.

4. The vector of claim 2, wherein said N-terminal truncation is S44.

* * * * *

SEQUENCE LISTING

```
<160> NUMBER OF SEQ ID NOS: 31

<210> SEQ ID NO 1
<211> LENGTH: 38
<212> TYPE: DNA
<213> ORGANISM: Haemophilus influenzae

<400> SEQUENCE: 1

ggccgcatat gaaaaaaaca cgttttgtac taaatagt                            38


<210> SEQ ID NO 2
<211> LENGTH: 10
<212> TYPE: PRT
<213> ORGANISM: Haemophilus influenzae

<400> SEQUENCE: 2

Met Lys Lys Thr Arg Phe Val Leu Asn Ser
  1               5                  10


<210> SEQ ID NO 3
<211> LENGTH: 36
<212> TYPE: DNA
<213> ORGANISM: Haemophilus influenzae

<400> SEQUENCE: 3

ttgttcggca aaacgatcgc caaagaagaa tttaaa                              36


<210> SEQ ID NO 4
<211> LENGTH: 36
<212> TYPE: DNA
<213> ORGANISM: Haemophilus influenzae

<400> SEQUENCE: 4

tttaaattct tctttggcga tcgttttgcc gaacaa                              36


<210> SEQ ID NO 5
<211> LENGTH: 12
<212> TYPE: PRT
<213> ORGANISM: Haemophilus influenzae

<400> SEQUENCE: 5

Phe Lys Phe Phe Phe Gly Asp Arg Phe Ala Glu Gln
```

-continued 1 5 10

<210> SEQ ID NO 6
<211> LENGTH: 38
<212> TYPE: DNA
<213> ORGANISM: Haemophilus influenzae

<400> SEQUENCE: 6
ggccgcatat gaaaaatata aaaagcagat taaaactc 38

<210> SEQ ID NO 7
<211> LENGTH: 10
<212> TYPE: PRT
<213> ORGANISM: Haemophilus influenzae

<400> SEQUENCE: 7

Met Lys Asn Ile Lys Ser Arg Leu Lys Leu
1 5 10

<210> SEQ ID NO 8
<211> LENGTH: 39
<212> TYPE: DNA
<213> ORGANISM: Haemophilus influenzae

<400> SEQUENCE: 8
tgccatattg aattcacgca aatcgaacca ctgacgacc 39

<210> SEQ ID NO 9
<211> LENGTH: 39
<212> TYPE: DNA
<213> ORGANISM: Haemophilus influenzae

<400> SEQUENCE: 9
ggtcgtcagt ggttcgattt gcgtgaattc aatatggca 39

<210> SEQ ID NO 10
<211> LENGTH: 13
<212> TYPE: PRT
<213> ORGANISM: Haemophilus influenzae

<400> SEQUENCE: 10

Gly Arg Gln Trp Phe Asp Leu Arg Glu Phe Asn Met Ala
1 5 10

<210> SEQ ID NO 11
<211> LENGTH: 69
<212> TYPE: DNA
<213> ORGANISM: Haemophilus influenzae

<400> SEQUENCE: 11
agcttagatg cttttgttgc tcgtcgcttt gcaaatgcca atagtgacaa tttgaatggc 60
aacaaaaaa 69

<210> SEQ ID NO 12
<211> LENGTH: 54
<212> TYPE: DNA
<213> ORGANISM: Haemophilus influenzae

<400> SEQUENCE: 12
cgcacaagct cacctacaac cttctggggt agattaacat tcagtttcta atag 54

<210> SEQ ID NO 13
<211> LENGTH: 39

-continued

<212> TYPE: PRT
<213> ORGANISM: Haemophilus influenzae

<400> SEQUENCE: 13

Ser Leu Asp Ala Phe Val Ala Arg Arg Phe Ala Asn Ala Asn Ser Asp
1 5 10 15

Asn Leu Asn Gly Asn Lys Lys Arg Thr Ser Ser Pro Thr Thr Phe Trp
20 25 30

Gly Arg Leu Thr Phe Ser Phe
35

<210> SEQ ID NO 14
<211> LENGTH: 47
<212> TYPE: DNA
<213> ORGANISM: Haemophilus influenzae

<400> SEQUENCE: 14
gatcctatta gaaactgaat gttaatctac cccagaaggt tgtaggt 47

<210> SEQ ID NO 15
<211> LENGTH: 76
<212> TYPE: DNA
<213> ORGANISM: Haemophilus influenzae

<400> SEQUENCE: 15
atctacgaaa acaacgagca gcgaaacgtt tacggttatc actgttaaac ttaccgttgt 60
tttttgcgtg ttcgag 76

<210> SEQ ID NO 16
<211> LENGTH: 38
<212> TYPE: DNA
<213> ORGANISM: Haemophilus influenzae

<400> SEQUENCE: 16
ggccgcatat gacaaaagaa aatttacaaa gtgttcca 38

<210> SEQ ID NO 17
<211> LENGTH: 10
<212> TYPE: PRT
<213> ORGANISM: Haemophilus influenzae

<400> SEQUENCE: 17

Met Thr Lys Glu Asn Leu Gln Ser Val Pro
1 5 10

<210> SEQ ID NO 18
<211> LENGTH: 36
<212> TYPE: DNA
<213> ORGANISM: Haemophilus influenzae

<400> SEQUENCE: 18
atagaatttt tctcgagcag caatcattga agttga 36

<210> SEQ ID NO 19
<211> LENGTH: 36
<212> TYPE: DNA
<213> ORGANISM: Haemophilus influenzae

<400> SEQUENCE: 19
tcaacttcaa tgattgctgc tcgagaaaaa ttctat 36

<210> SEQ ID NO 20

-continued

<211> LENGTH: 12
<212> TYPE: PRT
<213> ORGANISM: Haemophilus influenzae

<400> SEQUENCE: 20

```
Ser Thr Ser Met Ile Ala Ala Arg Glu Lys Phe Tyr
  1               5                  10
```

<210> SEQ ID NO 21
<211> LENGTH: 38
<212> TYPE: DNA
<213> ORGANISM: Haemophilus influenzae

<400> SEQUENCE: 21

```
agctttttac aggcgaccct cgtccattgg gcaaaata                            38
```

<210> SEQ ID NO 22
<211> LENGTH: 54
<212> TYPE: DNA
<213> ORGANISM: Haemophilus influenzae

<400> SEQUENCE: 22

```
ctgcttaaga aaacaaatga atggaagcgg aagcacttga gtaaaaaata atag          54
```

<210> SEQ ID NO 23
<211> LENGTH: 28
<212> TYPE: PRT
<213> ORGANISM: Haemophilus influenzae

<400> SEQUENCE: 23

```
Leu Phe Thr Gly Asp Pro Arg Pro Leu Gly Lys Ile Leu Leu Lys Lys
  1               5                  10                  15

Thr Asn Glu Trp Lys Arg Lys His Leu Ser Lys Lys
             20                  25
```

<210> SEQ ID NO 24
<211> LENGTH: 49
<212> TYPE: DNA
<213> ORGANISM: Haemophilus influenzae

<400> SEQUENCE: 24

```
gatcctatta ttttttactc aagtgcttcc gcttccattc atttgtttt                49
```

<210> SEQ ID NO 25
<211> LENGTH: 43
<212> TYPE: DNA
<213> ORGANISM: Haemophilus influenzae

<400> SEQUENCE: 25

```
aaaatgtccg ctgggagcag gtaacccgtt ttatgacgaa ttc                      43
```

<210> SEQ ID NO 26
<211> LENGTH: 41
<212> TYPE: DNA
<213> ORGANISM: Haemophilus influenzae

<400> SEQUENCE: 26

```
cgggatccca tatgaaaaaa ttaggtacat tactcgttct c                        41
```

<210> SEQ ID NO 27
<211> LENGTH: 10
<212> TYPE: PRT
<213> ORGANISM: Haemophilus influenzae -continued

```
<400> SEQUENCE: 27

Met Lys Lys Leu Gly Thr Leu Leu Val Leu
  1               5                  10


<210> SEQ ID NO 28
<211> LENGTH: 30
<212> TYPE: DNA
<213> ORGANISM: Haemophilus influenzae

<400> SEQUENCE: 28

ggccaagctt aaaaaacgcc agctcacatg                                       30


<210> SEQ ID NO 29
<211> LENGTH: 30
<212> TYPE: DNA
<213> ORGANISM: Haemophilus influenzae

<400> SEQUENCE: 29

catgtgagct ggcgtttttt aagcttggcc                                       30


<210> SEQ ID NO 30
<211> LENGTH: 38
<212> TYPE: DNA
<213> ORGANISM: Haemophilus influenzae

<400> SEQUENCE: 30

cgggatccca tatgtgtgct agcggaaaaa aagataca                              38


<210> SEQ ID NO 31
<211> LENGTH: 9
<212> TYPE: PRT
<213> ORGANISM: Haemophilus influenzae

<400> SEQUENCE: 31

Met Cys Ala Ser Gly Lys Lys Asp Thr
  1               5
```